US008158576B2

(12) United States Patent
Oppenheim

(10) Patent No.: US 8,158,576 B2
(45) Date of Patent: *Apr. 17, 2012

(54) VIRAL CAPSID PROTEINS AND ANY PEPTIDES OR COMPOSITIONS THEREOF FOR THE TREATMENT OF PATHOLOGIC DISORDERS

(75) Inventor: Ariella Oppenheim, Jerusalem (IL)

(73) Assignee: G.V.T. - Gene Vector Technologies Ltd., Jerusalem (IL)

(*) Notice: Subject to any disclaimer, the term of this patent is extended or adjusted under 35 U.S.C. 154(b) by 0 days.

This patent is subject to a terminal disclaimer.

(21) Appl. No.: 12/763,779

(22) Filed: Apr. 20, 2010

(65) Prior Publication Data

US 2010/0261655 A1    Oct. 14, 2010

Related U.S. Application Data

(62) Division of application No. 12/305,323, filed as application No. PCT/IL2007/000735 on Jun. 18, 2007, now Pat. No. 7,803,761.

(30) Foreign Application Priority Data

Jun. 18, 2006    (IL) .......................................... 176377

(51) Int. Cl.
    *C07K 14/00*    (2006.01)
(52) U.S. Cl. ........................................... 514/1; 530/350
(58) Field of Classification Search ....... 514/1; 530/350
    See application file for complete search history.

(56) References Cited

U.S. PATENT DOCUMENTS

| 6,090,608 | A  | 7/2000  | Oppenheim     |
| 6,238,859 | B1 | 5/2001  | Luke et al.   |
| 6,830,929 | B1 | 12/2004 | Sandalon      |
| 7,348,138 | B2 | 3/2008  | Weiner        |
| 7,803,761 | B2 | 9/2010  | Oppenheim     |
| 2004/0013647 | A1 | 1/2004 | Solomon et al. |
| 2010/0261655 | A1 | 10/2010 | Oppenheim    |
| 2010/0284974 | A1 | 11/2010 | Oppenheim    |

FOREIGN PATENT DOCUMENTS

DE    19750220 A1    5/1999
WO    2006046243 A1    5/2006

OTHER PUBLICATIONS

Chromy et al, PNAS 100, pp. 10477-10482, Sep. 2, 2003 "Chaperone-mediated in vitro assembly of Polymomavirus capsids."
Sandalon et al, "Self Assembly and Proteins-Protein Interactions between the SV40 Capsid Proteins Produced in Insect Cells", Virology, Oct. 1997, vol. 237, No. 2 pp. 414-421.
Sandalon, Z. and Oppenheim, A In SV40 protocols, L. Raptis, ed. (Totowa, NJ, Humana Press Inc.) (2001).
International Preliminary Report on Patentability published Mar. 17, 2009 for PCT/IL2007/000735, filed Jun. 18, 2007.
Written Opinion published on Mar. 13, 2009 for PCT/IL2007/000735, filed Jun. 18, 2007.
International Search Report published Apr. 30, 2009 for PCT/IL2007/000735, filed Jun. 18, 2007.
Li et al., J. Virol. 75 (16): 7321-7329 (2001).

Lenz et al: "Papillomavirus—Like Particles . . . Cells", Journal of Immunology, May 2001, vol. 166, No. 9, pp. 5346-5355.
Gordon-Shaag et al: "The Abundant Nuclear . . . Protein VP3", Journal of Virology, Apr. 2003, vol. 77, No. 1, pp. 4273-4282.
Yokoyama et al: "Mutational analysis of the carboxyl . . . protein VP1", Journal of Biochemistry, Feb. 2007, vol. 141, No. 2, pp. 279-286.
Georgens et al: "Recombinant virus like . . . system", Current Pharmaceutical Biotechnology, Feb. 2005, vol. 6, No. 1, pp. 49-55.
Aufricht, Christoph: "Heat-shock protein 70:molecular supertool?", Pediatric Nephrology, Jun. 2005, vol. 20, No. 6, pp. 707-713.
Sainis et al: "The hsc70 gene . . . gene family", FEBS Letters, Dec, vol. 355, No. 3, pp. 282-286, 1992.
Jo et al: "Heat preconditioning attenuates . . . injury", Journal of the American Society of Nephrology, Nov. 2006, vol. 17, No. 11, pp. 3082-3092.
Munther et al., Science's STKE 335:1-13 (2006).
Cripe et al., J. Virol. 69:7807-7813 (1995).
Sedjer et al., J. Virol. 68(7): 4685-4689 (1994).
Weiss et al., the J. Clin. Invest. 110:801-806 (2002).
Arad, U. Virology 304:155-159 (2002).
Roitman-Shemer, V. et al. Biochem Biophys. Res. Commun. 353:424-430 (2007).
Esterbauer, H. and Cheeseman, K.H. Methods Enzymol. 186:407-421 (1990).
Haverty, T.P. et al., Cell Biol. 107: 1359-1368 (1988).
Schmeer, C. et al. Restor Neurol Neurosci 24:79-95 (2006).
Fallon, L. et al. Nat. Cell. Biol. 8:834-842 (2006).
Cole, G.M. et al. Exp. Gerontol. 42:10-21 (2007).
Zhang, X. J. Cereb. Blood Flow Metab. 26:915-926 (2006).
Patten, R.D. and Karas, R.H. Trends Cardiovasc. Med. 16:69-75(2006).
Mitch, W.E. J. Ren. Nutr. 17:66-69 (2007). Bowie et al., Science 247, 1306-1310 (1990).
Schreiber et al., Nucleic Acids Research 17: 6419 (1989).
Lu, C.Y. et al. Curr. OP. in Nephrol. Hypertens. 16:83-89 (2007).
Riordan, M. et al. Nat. Clin. Pract. Nephrol. 2:149-156 (2006).
Kelly, K.j. Contrib. Nephrol. 148:86-106 (2005).
Gyrd-Hansen et al: "Heat Shock Protein . . . Integrity", Cell Cycle, vol. 3, No. 12, pp. 1484-1485 (Epub Dec. 2004).
Jarvis et al: "Heat Shock Protein . . . disease", Transplantation, vol. 76, No. 5, pp. 849-853, (Sep. 2003).
Office Action dated Jan. 11, 2011 for U.S. Appl. No. 12/772,550.
Magdalena Carlberg et al, "Short exposures to tunicamycin induce apoptosis in SV40-transformed but not in normal human fibroblasts", Carcinognesis Vo. 17, No. 12, pp. 2589-2596, 1996.
Crag D. Albright et al, Choline deficiency induces apoptosis in SV40-immortalized SWSV-1 rat hepatocytes in culture1, pp. 510516, vol. 10, Mar. 1996, The FASEB Journal.
Chicago Manual Style (CMS): Inactivation, Dictionary.com. The American Heritage® Stedman's Medical Dictionary, Houghton Mifflin Company, Jul. 6, 2011.

(Continued)

*Primary Examiner* — Karen Carlson
(74) *Attorney, Agent, or Firm* — Martin Fleit; Paul D. Bianco; Fleit Gibbons Gutman Bongini & Bianco PL

(57) ABSTRACT

The present invention relates to viral capsid proteins, as a medicament for the treatment of a pathologic disorder. More particularly, the invention relates to the viral capsid proteins VP1, VP2 and VP3, preferably, the SV40 VP1 or any peptide, fragment, mutant, derivative and mixtures thereof or of virus-like particles (VLP's) comprising the same, as the active ingredient in compositions for the treatment of pathologic disorders, preferably disorders associated with inactivation of cellular proteins involved with quality control processes, particularly, chaperones. The invention further provides methods for the treatment of such disorders and the use of the SV40 capsid proteins for the preparation of pharmaceutical compositions.

12 Claims, 12 Drawing Sheets

OTHER PUBLICATIONS

World English Dictionary, Collins English Dictionary. Complete & Unabridged 10th Edition 2009 © William Collins Sons & Co. Ltd., Cite This Source.

Database Buisus [Online] Biosciences Information Service, Philadelphia, PA, US; Apr. 2005; Cao Zeng et al; "Preparation of SV40 inactivation vaccine and immunization of Balb/c mice", XP002625274, Database accession No. PREV200510172154 *abstract* & Virologica Sinica, vol. 20, No. 2, Apr. 2005, pp. 159-163, 155, ISSN: 1003-5125.

Chromy Laura R. et al: "Chaperone-Mediated in Vitro Disassembly of Polyoma- and Papillomaviruses", Journal of Virology, vol. 80, No. 10, May 2006, pp. 5086-5091, XP002625275, ISSN: 0022-538X.

Butin-Israeli Veronika et al: "DNA-Free recombinant SV40 Capsids Protect Mice from Acute Renal Failure by Inducing Stress Response, Survival Pathway and Apoptotic Arrest", PLOS ONE, vol. 3, No. 8, Aug. 2008, XP002625276, ISSN: 1932-6203.

Evans Christoper G. et al: "Heat Shock Protein 70 (Hsp70) as an Emerging Drug Target", Journal of Medicinal Chemistry, vol. 53, No. 12, Jun. 2010, pp. 4585-4602, XP002625277, ISSN: 0022-2623, p. 4590, col. 1.

Supplementary European Search Report for EP07736471 issued by European Patent Office on Mar. 11, 2011.

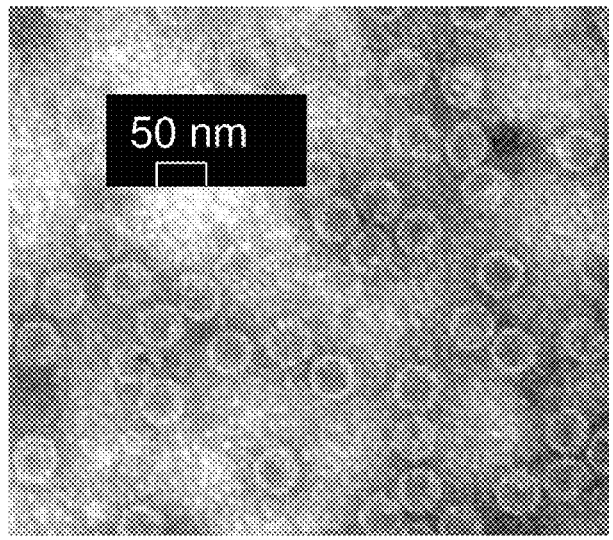
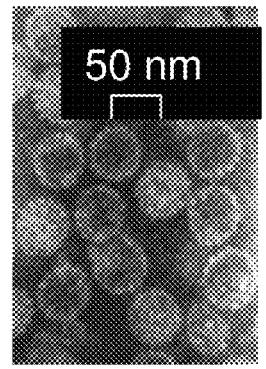
Fig. 1A
Fig. 1B
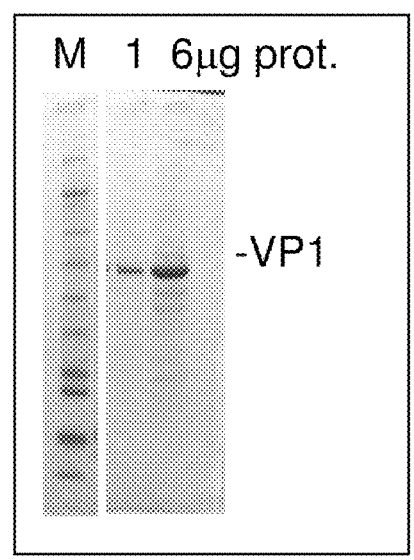
Fig. 1C

Cont.  Etoposide  Etoposide+VLPs

HgCl₂            HgCl₂ + VLPs

VIRAL CAPSID PROTEINS AND ANY PEPTIDES OR COMPOSITIONS THEREOF FOR THE TREATMENT OF PATHOLOGIC DISORDERS

FIELD OF THE INVENTION

The present invention relates to compositions and methods for treating disorders associated with inactivation of cellular proteins involved with quality control processes. More particularly, the invention relates to the use of viral capsid proteins, preferably, the SV40 VP1 or any peptide, fragment, mutant and mixture thereof in compositions and methods for the treatment of such pathologic disorders.

BACKGROUND OF THE INVENTION

All publications mentioned throughout this application are fully incorporated herein by reference, including all references cited therein.

Viruses, the ultimate parasites, usurp many cellular functions for their multiplication [Munther et al., Science's STKE 335:1-13 (2006)]. As soon as they bind to cells they trigger multiple cascades of events that they employ for cell entry, trafficking and disassembly, before they start utilizing cellular machinery for expression and replication. Some of the factors activated by the infecting virus participate in key processes such as inflammatory response and cell death.

The very early events that occur before disassembly and expression of the viral genome are most likely triggered by the viral outer shell. Thus viral capsids may be used to activate cellular mechanisms that may have therapeutic effects.

SV40 (and other members of the polyomavirus and papilloma virus families) induce chaperones following infection [Ioannis et al., FEBS Letters 355:282-286 (1994); Cripe et al., J. Virol. 69:7807-7813 (1995); Chromy et al., PNAS 100: 10477-10482 (2006) and references therein], presumably because they utilize host chaperons for disassembly (and assembly). As surprisingly shown by the present invention, chaperones are induced by the capsid proteins, or the viral structural proteins, rather than by viral regulatory proteins. Chaperons were proposed to ameliorate critical conditions such as ARDS (acute respiratory distress syndrome) and AKI (Acute Kidney Injury), which was previously referred to as ATN (acute tubular necrosis). In particular, ectopic expression of HSP70, applied by gene therapy to model ARDS rats, showed ameliorating effect [Weiss et al., the J. Clin. Invest. 110:801-806 (2002)]. Therefore, the inventors examined the possibility that induction of chaperones by SV40 may serve to treat these conditions. As clearly shown by the present invention, SV40 capsids (VLPs) remarkably ameliorated pathological symptoms using the AKI mice model, and are therefore applicable for use in the treatment of Acute Renal Failure (ARF). This particular example (ARF) clearly establishes the feasibility of using viral capsid proteins, and specifically the SV40 VP1, for treating any other disorders associated with disfunction of cellular quality control mechanisms, in variety of organs.

It is therefore one object of the invention to provide viral capsid proteins VP1, VP2 and VP3, preferably, the SV40 VP1 or any peptide, mutant, fragment and mixture thereof as the active ingredient in compositions for use in the treatment of pathologic disorders, preferably disorders associated with inactivation of cellular proteins. Such cellular proteins are preferably proteins involved with quality control processes, for example, chaperones.

In yet another object the invention provides methods for the treatment of disorders associated with inactivation of cellular proteins, preferably proteins involved with quality control processes, for example, chaperones.

Another object of the invention is to provide methods for enhancing the ameliorating effect of cellular proteins involved with quality control processes, for example, chaperones, on pathologic disorders, by augmenting these cellular proteins.

In another object, the invention provides the use of SV40 capsid proteins, or SV40 VLP's comprising said capsid proteins, in the preparation of compositions for the treatment of pathologic disorders, preferably, immune-related disorders or neurodegenerative disorders.

These and other objects of the invention will become apparent as the description proceeds.

SUMMARY OF THE INVENTION

In a first aspect the present invention relates to a pharmaceutical composition for the treatment of a pathologic disorder. The composition of the invention comprises as an active ingredient a therapeutically effective amount of at least one viral capsid protein or any peptide, mutant or fragment thereof, or any VLP's comprising at least one capsid protein or any peptide, mutant or fragment thereof.

It should be noted that the composition of the invention, although intended for the treatment of pathologic disorders, is not intended to be used as a vaccine against the virus in which said capsid proteins derived from.

According to one embodiment, the viral capsid protein may be any capsid proteins of papillomaviruses or polyomaviruses, or any fragment, peptide, mutant, any mixture and combinations thereof.

According to a specifically preferred embodiment, the viral capsid protein may be at least one of SV40 VP1, VP2, VP3, and any peptide, mutant, fragment, any mixture and any combinations thereof or any VLP's comprising at least one of said SV40 capsid proteins or any peptide, mutant or fragment thereof. Most preferably, the viral capsid protein may be SV40 VP1 or any peptide, mutant or fragment thereof. Particular example for a mutated SV40VP1 molecule may by the VP1ΔC mutant, preferably, said mutated molecule comprises the amino acid sequence substantially as denoted by SEQ ID NO. 4.

According to another embodiment, the composition of the invention may be particularly applicable and suitable for the treatment of a pathologic disorder such as a neurodegenerative disorder or an immune-related disorder. It should be noted that the pathologic disorder to be treated by the composition of the invention is preferably a disorder associated with inactivation of cellular proteins involved with quality control processes within the cell, preferably, a disorder associated with inactivation of chaperones.

In a second aspect, the present invention relates to a method for the treatment of a pathologic disorder in a subject in need thereof. This method comprises the step of administering to the treated subject a therapeutically effective amount of at least one viral capsid protein or any peptide, mutant or fragment thereof or any VLP's comprising the same, or of a composition comprising the same.

In a third aspect, the invention relates to a method for enhancing the ameliorating effect of cellular proteins participating on quality control processes, on a pathologic disorder. This method comprises the steps of contacting cells obtained from a subject suffering of a pathologic disorder with an effective amount of at least one viral capsid protein or any peptide, mutant or fragment thereof, or of VLP's comprising the same.

In a fourth aspect, the invention relates to the use of at least one viral capsid protein or any peptide, mutant or fragment thereof or VLP's comprising the same, in the preparation of a pharmaceutical composition for the treatment of a pathologic disorder.

The invention will be further described on hand of the following figures and examples.

BRIEF DESCRIPTION OF THE FIGURES

FIG. 1A-1C. Production of Recombinant VLPs in Insect Cells (A) VLPs and (B) wild-type SV40, viewed under the electron microscope following staining in 1% phospho tungstate, pH 7. (C) PAGE analysis of the purified VLPs, stained by Coomassie. Abbreviations: Prot. (protein).

CV1 cells were treated with SV40 VLPs, 50 ng and 500 ng per $10^6$ cells. (A) Total cell proteins were harvested at different time points, shown in hours above, and analyzed by Western blotting with monoclonal antibodies against hsp/hsc70 proteins. Controls: HS—CV1 cells, heat shocked for 90 min at 45° C., C—untreated control. (B) CV1 cells treated with 50 ng VLPs, immunostained with anti-Hsp/c 70 antibody and viewed under confocal microscopy. Abbreviations: moc. (mock).

Figure 3A:
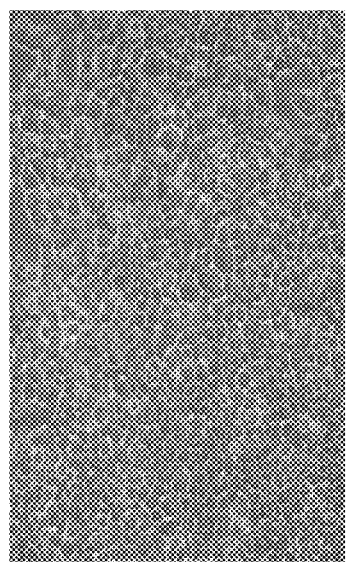
Figure 3B:
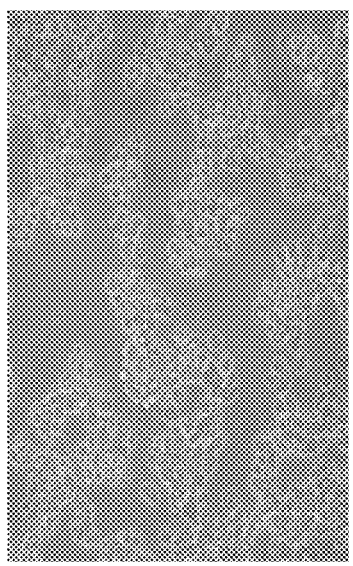
Figure 3C:
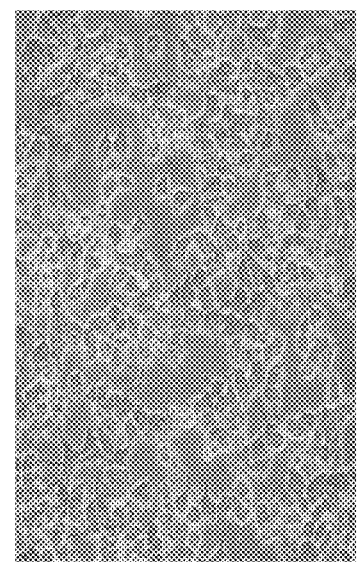

FIG. 3A-3C. Embryonic Human Kidney (HEK) Cells

Cells were treated with etoposide at the time of infection with VLPs, at a final concentration of 20 μg/ml. The concentration of VLPs was 50 ng per $10^6$ cells. (A) shows control; (B) shows treatment with etoposide and (C) shows treatment with etoposide and SV40 VPL's. Abbreviations: cont. (control).

Figures 4A, 4B:
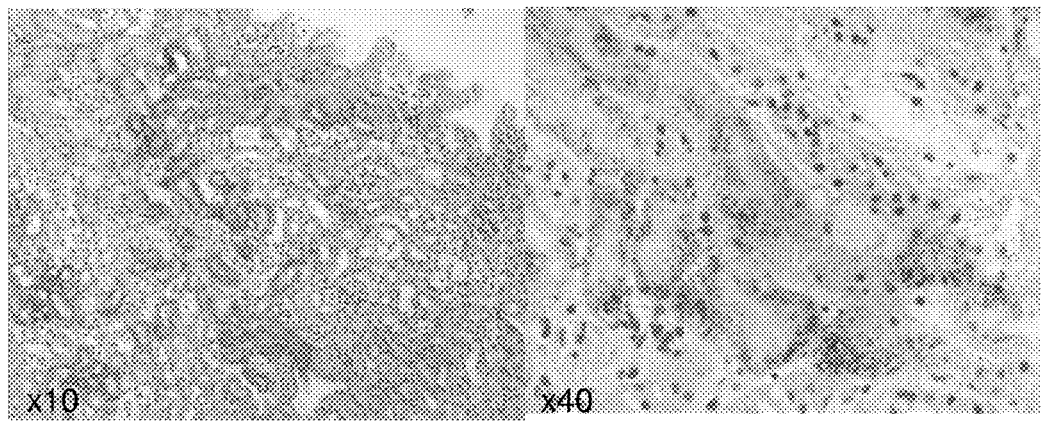

FIG. 4A-4B. SV40 Targets the Kidney in Mice

A section through the kidney of a mouse 48 hours following injection with $10^8$ infectious units (pfu) of SV luc vector [Arad, U. Virology 304:155-159 (2002)] in 100 μl volume via the tail vein. Immunohistochemistry was performed on renal tissue with an anti-SV40 VP1 [Sandalon and Oppenheim, Virology 237:414-421 (1997)] as the primary antibody and an HRP-labeled anti-rabbit secondary antibody. Brown stain indicates VP1 uptake by renal tubular epithelial cells. PBS injected controls did not show staining. (A) shows 10× magnification and (B) shows 40× magnification.

Figure 5:
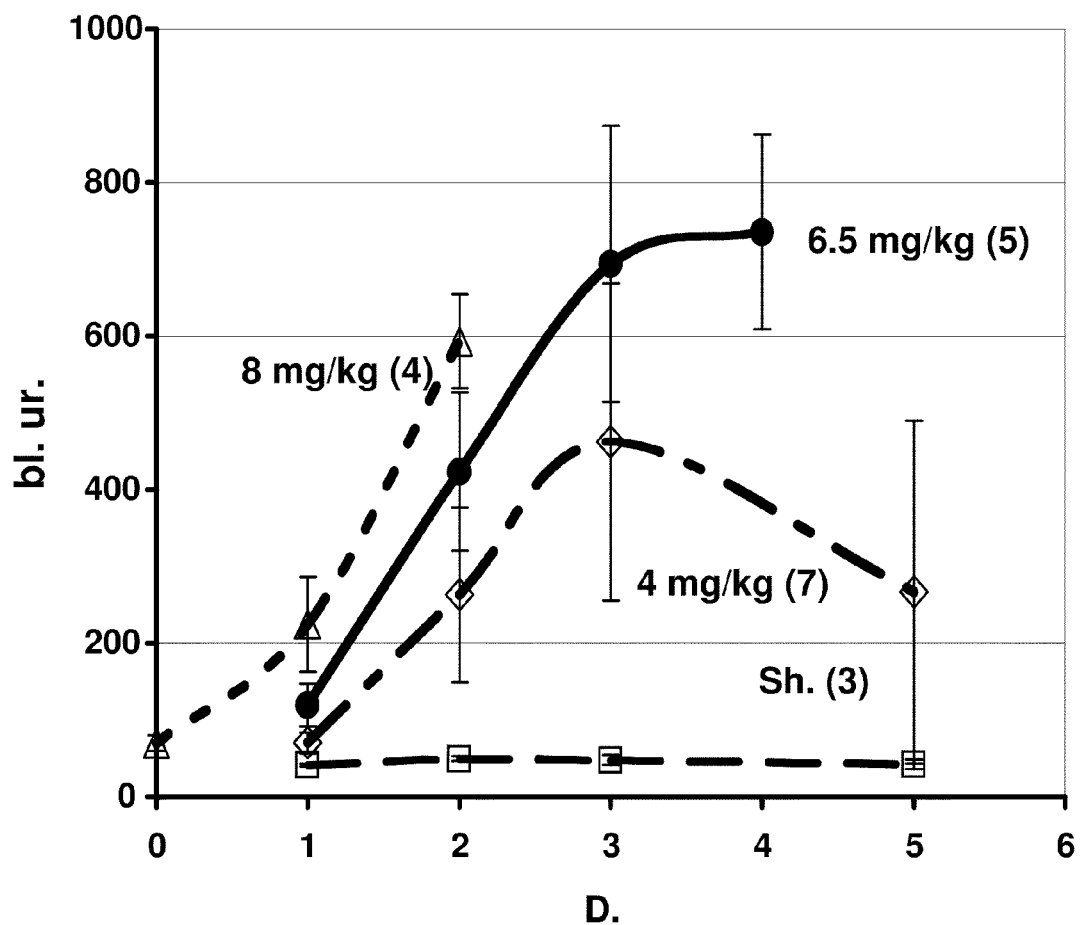

FIG. 5. Mouse Model of Nephrotoxicity $HgCl_2$, at the designated concentration, was administered IP to BALB/C female mice, blood was drawn from the tail-vein on the designated day and urea levels were measured using Reflotron urea test (Roche). The number of animals in each group is shown in parentheses. The bars represent standard deviation. Abbreviations: bl. Ur. (blood urea), sh. (sham).

Figure 6A:
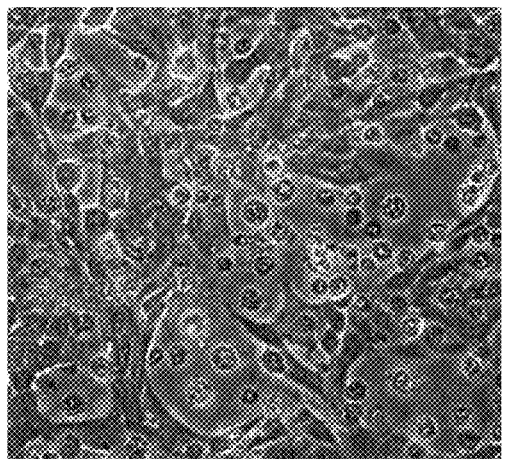
Figure 6B:
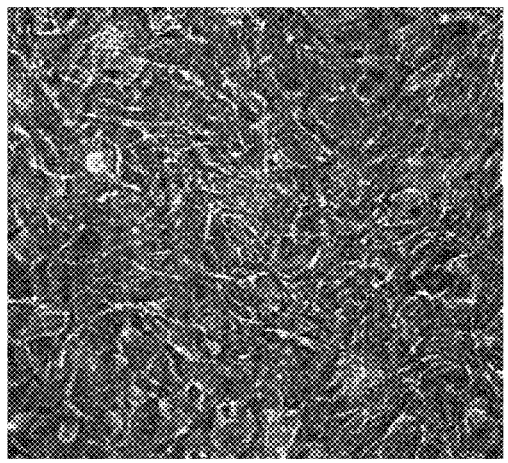

FIG. 6. Protection of Cultured Mouse Tubular Kidney Cells Against $HgCl_2$ Insult Cultured mouse tubular kidney cells were treated with $HgCl_2$ (A) or $HgCl_2$ and SV40 VLP's (B), and viewed under the microscope.

Figure 7A:
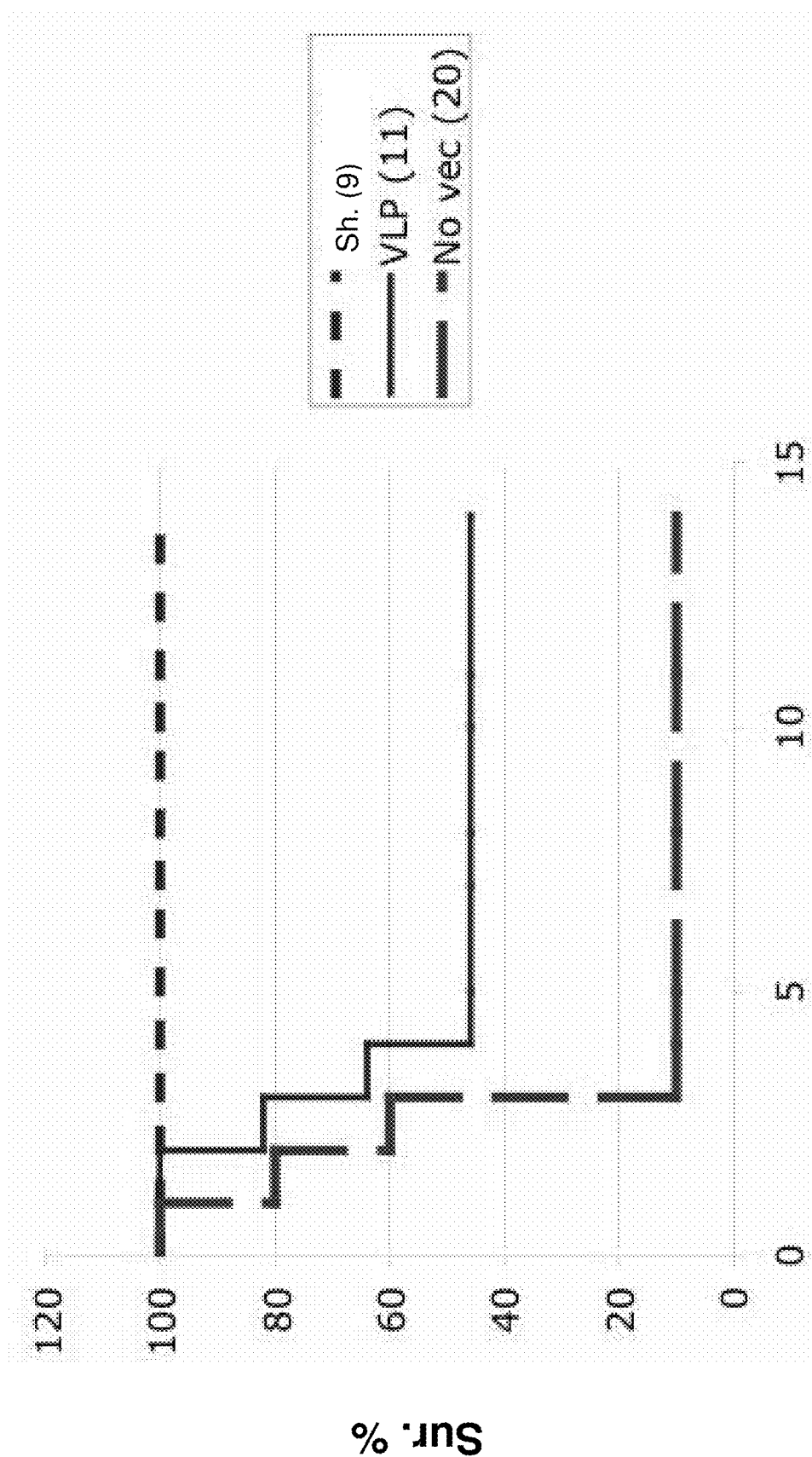
Figure 7B:
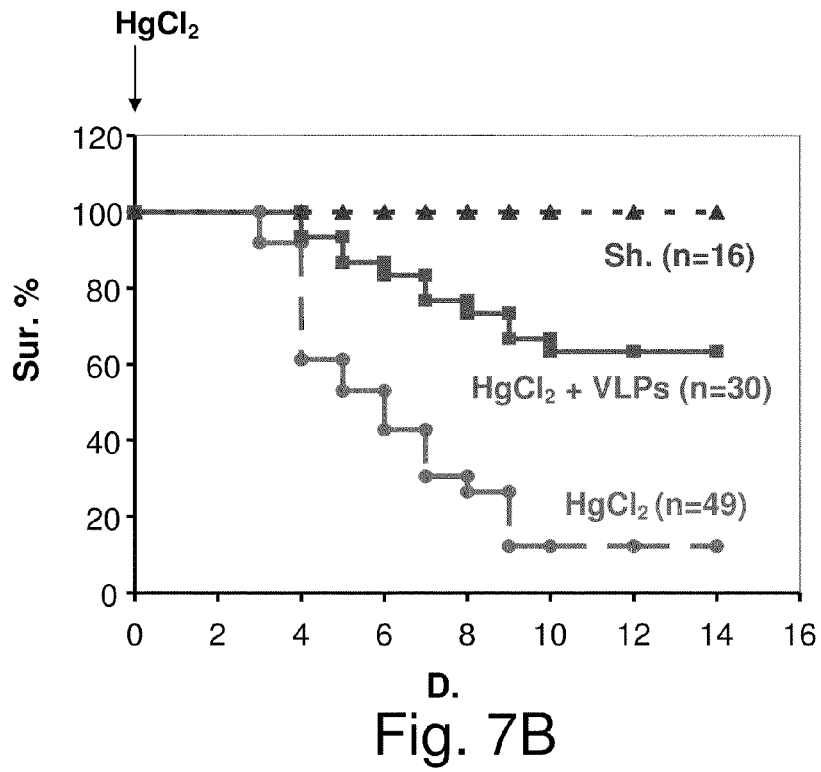
Figure 7C:
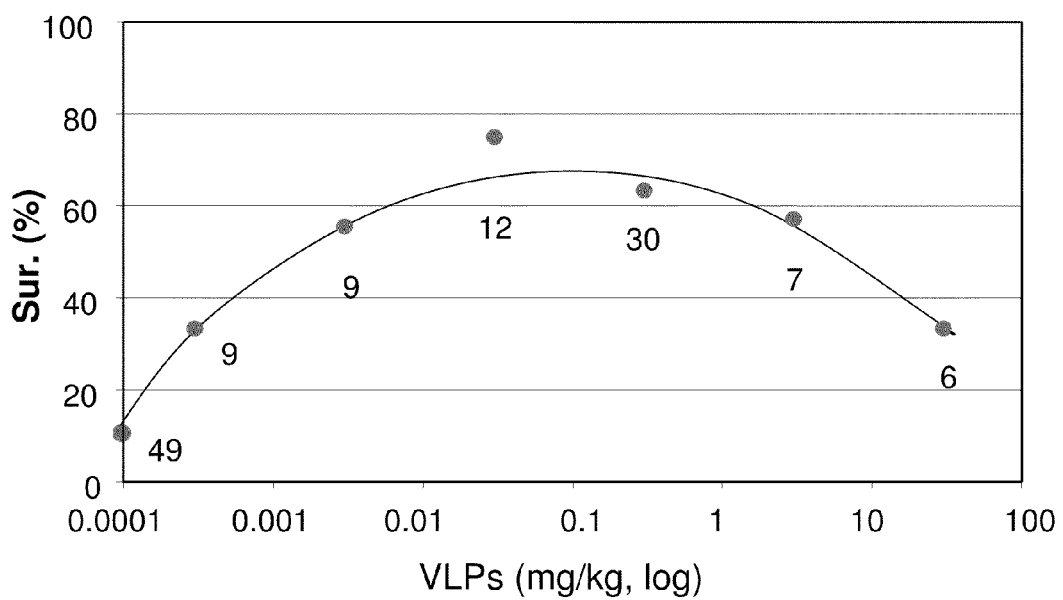

FIG. 7A-7C. Survival Rate of Mice Treated with SV40 VLP's (A) The figure shows that treatment with VLPs increases the survival rate of AKI model mice (No vec.=$HgCl_2$ only; VLP=VLP+$HgCl_2$); (B) shows survival of the VLP-treated vs, untreated AKI animals; (C) shows dose response. Note log scale of the VLP dose. The numbers below the points designate the number of animals at the particular dose. Abbreviations: sur. (survival), D (days post $HgCl_2$ injection), sh. (sham).

Figure 8A:
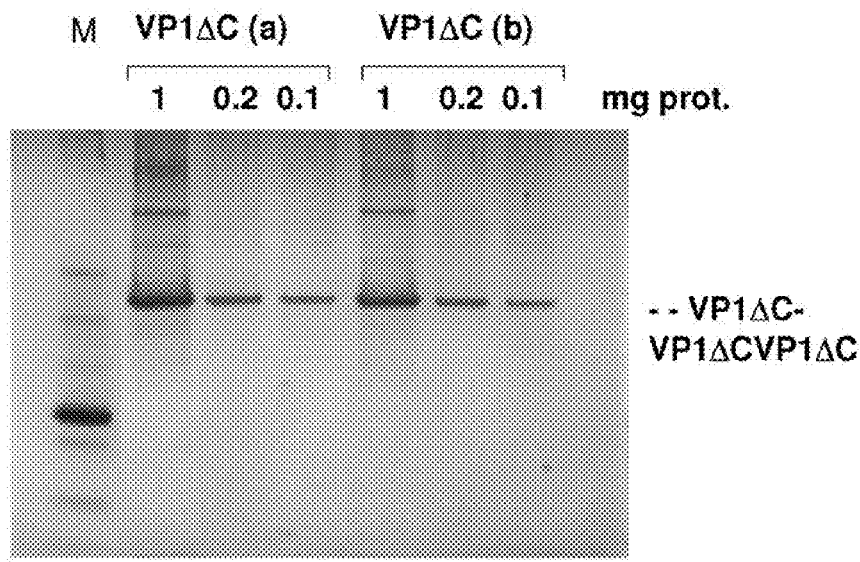
Figure 8B:
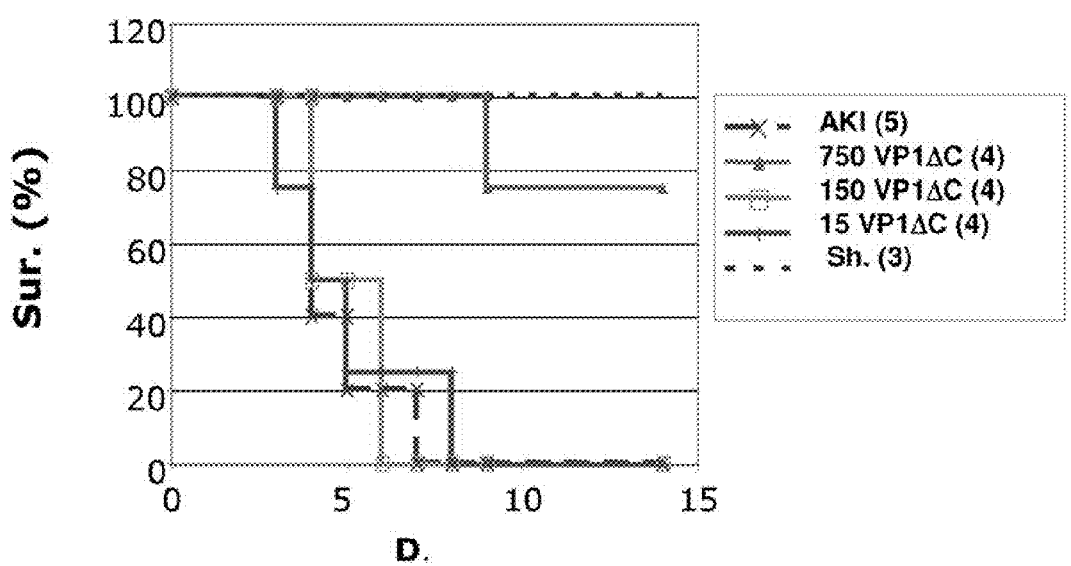

FIG. 8A-8B. Mutated SV40 VP1 Capsid Protein, VP1ΔC Protects AKI Mice (A) Production of the mutant protein (a), (b)—samples from two different batches of VP1ΔC that were injected to mice. PAGE was run in MES buffer and proteins detected by silver staining. M-SeeBlue size marker (Invitrogen). (B) Survival experiments. Abbreviations: Prot. (protein), Sur. (survival), sh. (sham).

Figure 9A:
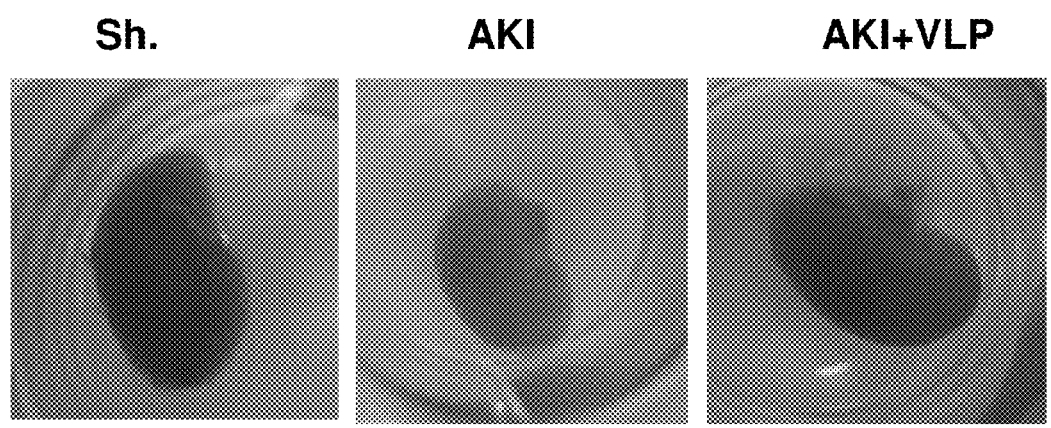
Figure 9B:
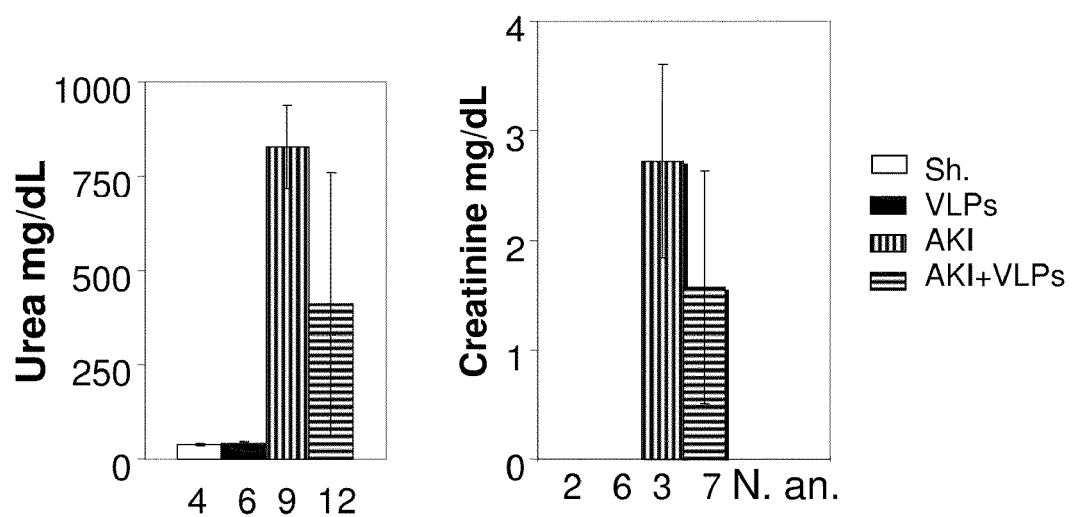
Figure 9C:
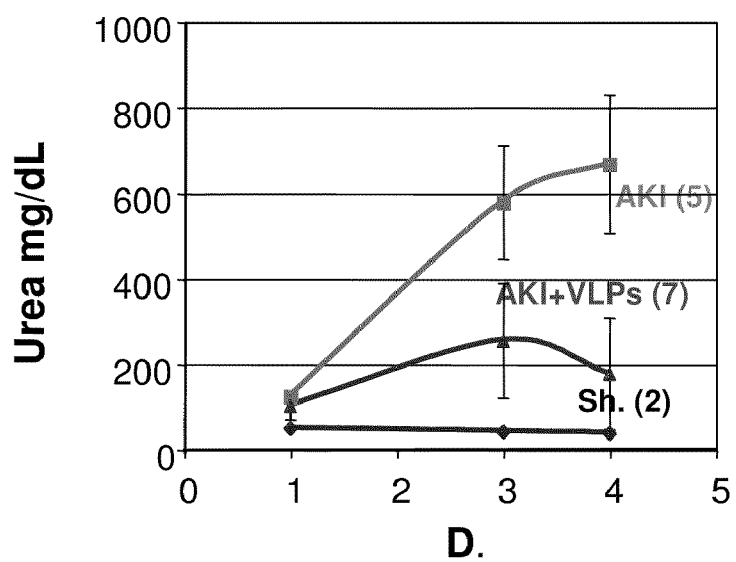

FIG. 9A-9C. SV40 VLP's Protective Effect in Different Disease Parameters (A) Kidney gross appearance as photographed 3 days after $HgCl_2$ injection. (B) Serum urea (left) and creatinine (right) levels were measured on day 4 using Reflotron kit for urea and creatinine tests (Roche) respectively. Note that serum creatinine in the sham and VLP-only treated groups was below detection level. Results of one-tailed Student's t-Test were P=0.0008 for blood urea and P=0.035 for creatinine. The numbers of animals in each group is designated below. (C) Serum urea of VLP-treated AKI and non-treated AKI mice. The number of animals in each group is shown in parentheses. Bars represent standard error. Abbreviations: N. an (number of animals), D. (days), sh. (sham).

Figure 10:
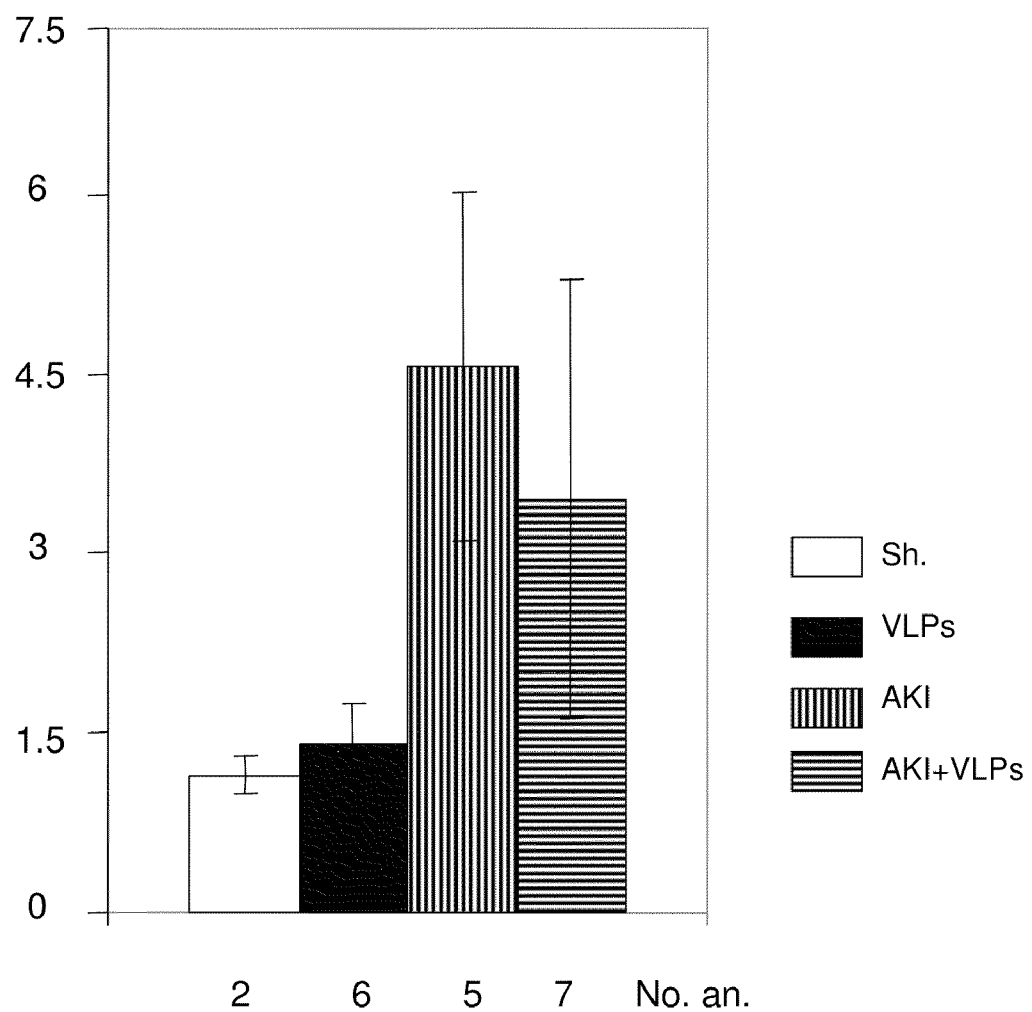

FIG. 10. Mercury-Induced Oxidative Stress

Levels of thiobarbituric acid reactive substances were measured using TBARS assay [Esterbauer, H. and Cheeseman, K. H. Methods Enzymol. 186:407-421 (1990)]. Mice were injected with 6.5 mg/kg $HgCl_2$, with or without treatment with 0.3 mg/kg VLPs. The number in each group is shown below the bars. Abbreviations: N. an (number of animals), sh. (sham).

DETAILED DESCRIPTION OF THE INVENTION

In a first aspect, the present invention relates to a pharmaceutical composition for the treatment of a pathologic disorder. The composition of the invention comprises as an active ingredient a therapeutically effective amount of at least one viral capsid protein or any peptide, mutant or fragment thereof or of VLP's comprising at least one capsid protein or any peptide, mutant or fragment thereof.

It should be noted that the composition of the invention, although intended for the treatment of pathologic disorders, is not to be used as a vaccine against the virus in which said capsid proteins derived from. Therefore, the composition of the invention is for the treatment of a pathologic disorder, provided that, this composition is not used as a vaccine or for vaccination of the treated subject.

According to one embodiment, the viral capsid protein comprised as an active ingredient may be any one of the capsid proteins of papillomaviruses or polyomaviruses, or any fragment, peptides and mixtures and combinations thereof.

The papilloma, polyoma, and vacuolating agents seem to form a natural group of tumor viruses, for which the name papova virus group was used. Historically, the name papova was derived from Rabbit PApilloma virus, Mouse POlyoma virus, Simian VAcuolating virus. Members of the group are all non-enveloped viruses having double stranded DNA genome, which perform multiplication within the cell nucleus. Papilloma and polyomaviruses are related virus families with a common capsid architecture. For both, 72 capsomeres, each a pentamer of the major capsid protein, form a T=7 icosahedral lattice. This structural similarity exists despite a complete lack of sequence homology between polyomavirus (VP1) and papillomavirus (L1) major capsid proteins.

Seventy strains of Human Papillomavirus (HPV) have been identified so far. These viruses are known for their role in causing warts (both common warts and genital warts) as well as their association with cancer. Most people are infected with some strain of HPV in their lives. Two structural proteins form the capsids of papillomaviruses. The major structural protein L1 is the structural determinant of the capsids and is present in 360 copies arranged in 72 pentamers. The minor structural protein L2 is estimated to be present in 12 copies per capsid. Possible roles for L2 in interaction with cell surface receptors and in virion uptake have been suggested. L2 localizes in sub-nuclear domains identified as nuclear domain 10 (ND10).

Therefore, according to a particular embodiment, the papillomavirus capsid proteins L1 and L2 may be used as an active ingredient for the composition of the invention. The Polyomaviridae family of small, nonenveloped, icosahedral DNA viruses may be best represented by the murine polyomavirus, the simian virus 40 (SV40), human BK virus and human JC virus. Like most DNA viruses, polyomavirus capsid proteins are synthesized in the cytosol, whereas assembly of virions occurs only in the nucleus. Polyomavirus capsids are comprised of 72 pentamers (capsomeres) of the major capsid viral protein (VP1), which is arranged in a T=7 icosahedral lattice ≈50 nm in diameter. One minor capsid protein, either VP2 or VP3, binds in the central 5-fold cavity of each VP1 either VP2 or VP3, binds in the central 5-fold cavity of each VP1 pentamer. The atomic structure of the virion reveals that the C-terminal domain of each VP1 monomer "invades" a neighboring pentamer to form the principal interpentamer contacts, and these contacts are stabilized by calcium ions.

According to a specifically preferred embodiment, the viral capsid protein may be at least one of SV40 VP1, VP2, VP3, and any peptide, mutant, fragments, mixtures and combinations thereof or VLP's comprising at least one of SV40 VP1, VP2, VP3, or any peptide, mutant or fragment thereof. Most preferably, the viral capsid protein may be SV40 VP1 or any peptide, mutant or fragment thereof. It should be noted that preferably the term SV40 VP1 protein refers to the VP1 protein having the amino acid sequence as indicated by GenBank Accession number NP_043126 GI: 96 28426, which is incorporated herein by reference. According to a specifically preferred embodiment, the SV40 VP1 capsid protein comprises the amino acid sequence as denoted by SEQ ID NO:1.

SV40 is a small, double-stranded DNA Primate polyomavirus with a mini chromosome of 5.2 kb. The viral capsid is composed of three viral-encoded proteins, VP1, VP2, and VP3, that encloses the minichromosome. Encapsidation occurs by gradual addition and organization of capsid proteins around the chromatin. The viral proteins VP2 and VP3 are thought to bridge between the viral chromatin and the VP1 capsid shell. A domain near the carboxyl-terminus of VP3 has been shown to interact in vitro with VP1. An additional viral late protein is the agnoprotein, or LP1, coded by the leader region of the late 16S mRNA. This small (61 amino acids) protein was found to mediate efficient localization of VP1 to the nuclear region and to facilitate release of mature virus from the infected cells.

It should be appreciated that any mutated viral capsid protein, preferably, VP1 molecule, which posses enhancing effect on chaperons levels, enhancement of cell survival mechanisms and rescuing cells from apoptosis or oxidative stress, is encompassed by the present invention.

The viral capsid protein mutants or derivatives thereof that may be used by the compositions and method of the invention may have at least one mutation selected from the group consisting of point mutations, missense, nonsense, insertions, deletions or rearrangement. It should be appreciated that the terms "insertions" and "deletions" as used herein is meant any addition or deletions, respectively, of amino acid residues to the viral capsid proteins of the invention, between 1 to 100 amino acid residues, preferably, between 1 to 50 amino acid residues and most preferably, between 1 to 20 amino acid residues.

According to one particular embodiment, a mutated SV40 VP1 molecule may be a VP1 molecule deleted in its carboxy terminal arm. Such particular mutated molecule may be the mutant VP1ΔC. According to a particularly preferred embodiment, this mutated VP1 molecule comprises the amino acid sequence substantially as denoted by SEQ ID NO. 4.

It should be appreciated that additional mutations, including deletion or insertions, may be, for example, in the surface loops of VP1 which connect between the β-strands, are within the scope of the invention. Such mutations are expected to be more potent than wild type VP1 in activating the chaperon machinery and/or survival pathway, as well as protecting cells against apoptosis or oxidative stress. It should be further noted that any other mutations affecting the structure of VP1, or VP1 derivative, allowing it to have a prolonged effect in vivo, are also within the scope of the present invention.

According to a particular embodiment, the compositions of the invention may comprise any combination of wild type VP1, the VP1ΔC mutant and any other mutant described above.

It should be noted that the viral capsid proteins used in the composition and methods of the invention can be natural or synthetic, modified or unmodified, whole or fragments thereof. Fragments can be derived from synthesis as fragments or by digestion or other means of modification to create fragments from larger entities.

Preferably, the viral capsid proteins may be recombinantly prepared. Preparation of recombinant capsid proteins involves the use of general molecular biology techniques that are well known in the art. Such techniques include for example, cloning of the gene encoding a desired viral capsid protein to a suitable expression vector. Preferred recombinant SV40 VP1 capsid proteins may be prepared using prokaryotic, preferably, bacterial or eukaryotic expression systems. Most preferred are capsid proteins prepared in eukaryotic expression system, such as the baculovirusdes system described in Experimental procedures. It should be noted that construction of these vectors is also described in detail in Sandalon et al., [Sandalon (1997) ibid.], which is a previous publication by the inventor and is incorporated herein by reference.

It should be further noted that the capsid proteins and specifically the SV40 VP1, may be used for the composition of the invention as dissociated VP1 pentamers or as virus-like particles (VLP's, as demonstrated by FIG. 1) comprising VP1 and other SV40 capsid proteins or alternatively, containing VP1 only. Still further, it should be appreciated that the viral capsid proteins may be mixed with any other viral protein such as the agnoprotein or any other protein facilitating their action. Still further, it should be noted that for preparation of dissociated pentamers or fragments of said SV40 VP1 protein, a bacterial expression system may be used. Moreover, it should be appreciated that the invention further encompasses the use of any fusion protein comprising said VP1, or any mutant of VP1 (for example, the VP1ΔC), as an active ingredient in any one the compositions of the invention.

According to a specifically preferred embodiment, the pathologic disorder to be treated with the composition of the invention, may be associated with inactivation of cellular proteins participating in quality control processes and therefore may be ameliorated by activation of such proteins.

Newly synthesized proteins have a string-like structure, and the strings must be adequately folded sterically so that the resultant proteins work normally. For this purpose, molecules called "molecular chaperons" exist in the endoplasmic reticula to help sterically adequate folding of the protein strings. However, proteins are sometimes not adequately folded even with the molecular chaperon's help. Such unusual proteins are excluded from the endoplasmic reticula (ER) and decomposed in a protein-degradation factory called "proteasome." That is, the endoplasmic reticulum possesses a function to distinguish inadequately folded proteins from folded ones in order to dispose of the unusual proteins. This functional mechanism is referred to as the "quality-control mechanism of proteins in the endoplasmic reticulum." If this mechanism is broken, cells cannot judge which proteins are adequate "products," inducing severe, life-threatening damage.

More specifically, in living cells, both newly made and preexisting polypeptide chains are at constant risk for misfolding and aggregation. In accordance with the wide diversity of misfolded forms, elaborate quality-control strategies have evolved to counter these inevitable mishaps. Recent reports describe the removal of aggregates from the cytosol, reveal mechanisms for protein quality control in the endoplasmic reticulum, and provide new insight into two classes of molecular chaperones, the Hsp70 system and the AAA+ (Hsp100) unfoldases.

As indicated above, the endoplasmic reticulum (ER) is responsible for the structural maturation of the roughly one-quarter of the proteome that traverses the secretory pathway. The ER employs two distinct mechanisms for responding to the presence of misfolded forms. The first is an ER-dedicated stress response termed the unfolded protein response (UPR), which acts to remodel the ER so as to increase its folding capacity. In yeast, the folding capacity of the ER is monitored by IRE1, a highly conserved transmembrane kinase that contains a lumenal domain responsible for sensing misfolded forms and cytosolic kinase and ribonuclease domains. The accumulation of misfolded proteins in the ER leads to activation of the IRE kinase.

The second, termed ER-associated degradation (ERAD), specifically recognizes terminally misfolded proteins and retrotranslocates them across the ER membrane into the cytosol, where they can be degraded by the ubiquitin-proteasome degradation machinery. As might be expected by the diversity of proteins that fold in the ER, recent studies argue that ER-associated degradation (ERAD) encompasses a number of different systems, each responsible for the degradation of subsets of proteins that share common physical properties. This is perhaps most clearly shown in yeast, where there are at least two distinct surveillance mechanisms for identifying terminally misfolded ER proteins. The first, designated ERAD-L, inspects for proteins that contain misfolded lumenal domains. The second, termed ERAD-C, detects misfolded cytosolic domains of transmembrane proteins. Although both of these pathways ultimately converge on the ubiquitin-proteasome degradation system, they depend on different sets of ER-associated components to detect and deliver misfolded species to the cytosol. In the case of ERAD-C (but not ERAD-L), degradation is typically dependent on a specific subset of cytosolic chaperones including Hsp70 and Hsp40 members.

Recent studies have identified two different ER-localized lectins that play a critical role in ERAD. The first is related to the mannosidase protein responsible for the trimming of N-glycans in the ER but appears to have lost its catalytic activity. The second lectin, Yos9p, forms a stable complex with misfolded proteins, and loss of Yos9p leads to a profound and specific defect in degradation of misfolded glycoproteins.

The ubiquitin-proteasome pathway might be the mainstay of removal of aggregation-prone species. It appears now that ubiquitin modification may in fact recruit aggregated species for clearance via an independent mechanism, the "autophagy" pathway. Autophagy involves the recognition and packaging/engulfment of targeted proteins or organelles into autophagosome vesicles that become fused with lysosomes, wherein both vesicles and their contents are broken down. More than 20 so-called Atg components mediate this remarkable process.

It has become increasingly apparent that there are a variety of conditions in vivo where, even with chaperones and the proteolytic machinery present in the same compartment as a misfolding protein, these mechanisms of quality control fail and the misfolded proteins proceed to form aggregates. Moreover, such intracellular aggregates are associated with a number of neurodegenerative diseases such as Huntington's, Alzheimer's, Amyotrophic lateral sclerosis and Parkinson's. The nature and fate of protein aggregates in eukaryotic cells has been poorly understood.

Without being bound by any theory, as shown by the following Examples, the viral capsid proteins, particularly, VLPs containing VP1, VP1 pentamers or mutated VP1 molecule, preferably, the VP1ΔC mutant, activated proteins participating in quality control processes, specifically, chaperones (as shown by the present invention for HSP/c70, for example), and thereby led to clear amelioration of the pathologic condition treated. This amelioration of a pathologic condition was clearly demonstrated by the invention using the AKI (acute kidney injury) mice model, which was formally referred to as ATN.

Therefore, according to a specific embodiment, proteins participating in quality control processes may be chaperones. For example, chaperones of the following families: HSP-40, HSP-70, CALNEXIN, BiP, HSP-27, HSP-22, HSP-60, HSP-65, HSP-27, HSP-90.

Heat shock proteins (HSPs) are called stress proteins or molecular chaperons that assist cell rescue through the folding of synthesized or stress-denatured proteins. As indicated above, HSPs are also believed to be causative factors in various autoimmune diseases, whose etiologies are considered to spring from immune responses against HSPs as a target molecule. For instance, elevated antibody titers to HSP60 family proteins as well as the HSP70 family proteins (HSP70 and HSC70), are reported in cerebrospinal fluid (CSF) of patients with multiple sclerosis (MS) and other neurological diseases, and therefore may play an important role in the pathophysiology of MS through the modification of immune response and cytoprotective functions of molecular chaperons.

Mutations of the heat shock proteins 27 (HSP27) and HSP22, were identified in Charcot-Marie-Tooth disease (CMT), which is one of the most common but heterogeneously hereditary motor and sensory neuropathy and in distal hereditary motor neuropathy (HMN) which is an exclusively motor neuropathy but is also a clinically and genetically heterogenous neuropathy.

Acute Respiratory Distress Syndrom (ARDS) (an example for inflammatory response), Legioner disease, GBS (Guillain-Barre Syndrom) and podocyte injury, are also disorders shown to be associated with disfunction of chaperones, and are therefore conditions that may be treated by the compositions and methods of the invention.

According to another embodiment, the composition of the invention may be particularly applicable and suitable for the treatment of pathologic disorders such as neurodegenerative disorders or immune-related disorders. It should be noted that, as indicated above, the pathologic disorder to be treated by the composition of the invention is preferably a disorder associated with inactivation of cellular proteins involved with quality control processes within the cell.

More specifically, immune disorders related to an imbalance in the Th1-Th2 response and therefore, an immune-related disorder may be for example, an autoimmune disease, (for example, multiple sclerosis (MS), Type-1 diabetes, lupus, Graves disease and thyroiditis), malignant and non-malignant proliferative disorders, graft rejection pathology and graft versus host disease, inflammation and also pathogen related disorders (such as toxic shock, incapacitation and death, septic shock and severe sepsis, induced by a pyrogenic exotoxin).

Inflammation includes any inflammatory conditions wherein said inflammatory conditions may be any one of rheumatoid arthritis, acute respiratory distress syndrome (ARDS), asthma, rhinitis, idiopathic pulmonary fibrosis, peritonitis, cardiovascular inflammation, myocardial ischemia, reperfusion injury, atherosclerosis, sepsis, trauma, diabetes type II, retinopathy, psoriasis, gastrointestinal inflammation, cirrhosis and inflammatory bowel disease.

In general, the compositions as well as the methods of the present invention described herein below, may be used in the treatment of any autoimmune disease such as for example, but not limited to, Eaton-Lambert syndrome, Goodpasture's syndrome, Greave's disease, Guillain-Barr syndrome, autoimmune hemolytic anemia (AIHA), hepatitis, insulin-dependent diabetes mellitus (IDDM), systemic lupus erythematosus (SLE), multiple sclerosis (MS), myasthenia gravis, plexus disorders e.g. acute brachial neuritis, polyglandular deficiency syndrome, primary biliary cirrhosis, rheumatoid arthritis, scleroderma, thrombocytopenia, thyroiditis e.g. Hashimoto's disease, Sjogren's syndrome, allergic purpura, psoriasis, mixed connective tissue disease, polymyositis, dermatomyositis, vasculitis, polyarteritis nodosa, polymyalgia rheumatica, Wegener's granulomatosis, Reiter's syndrome, Behget's syndrome, ankylosing spondylitis, pemphigus, bullous pemphigoid, dermatitis herpetiformis, insulin dependent diabetes, inflammatory bowel disease, ulcerative colitis and Crohn's disease.

As used herein to describe the present invention, the terms "malignant proliferative disorder", "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the composition as well as the methods of the present invention described below, may be used in the treatment of non-solid and solid tumors, for example, carcinoma, melanoma, leukemia, and lymphoma.

Therefore, according to a preferred embodiment, the SV40 capsid proteins or any composition comprising the same according to the invention, can be used for the treatment or inhibition of non-solid cancers, e.g. hematopoietic malignancies such as all types of leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma, as well as for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of Vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma.

In yet another specific embodiment, the compositions of the invention as well as the methods of the invention described herein after, may be used for the treatment of a neurodegenerative disorder.

A "neurological disorder" is a disease or disorder characterized by an abnormality or malfunction of neuronal cells or neuronal support cells. The disorder can affect the central and/or peripheral nervous system. Exemplary neurological diseases include neuropathies, skeletal muscle atrophy and neurodegenerative diseases.

"Neurodegenerative disorders" are complex and pernicious diseases, their onset is insidious, followed by progressive deterioration. Clinical manifestations are determined by the location and seriousness of the disorder. Although the causes may differ, patients with neurodegenerative disorders are likely to show localized to generalized atrophy of brain cells, leading to compromises in both mental and physical function. Exemplary neurodegenerative diseases include: Alzheimer's disease, Parkinson's disease, ALS (Amyotrophic Lateral Sclerosis), Huntington's disease, taupathies such as Pick's disease, fronto temporal dementia, corticobasal degeneration and progressive supranuclear palsy and Spongiform encephalopathies such as Scrapie, mad cow disease and Bovine spongiform encephalopathy, Creutzfeldt-Jakob disease, Fatal Familial Insomnia, Gerstmann-Straussler-Scheinker syndrome and Kuru.

As indicated above, the pathologic disorder treated by the composition of the invention may be a disorder induced by a pathogenic agent. Pathogenic agents include prokaryotic microorganisms, lower eukaryotic microorganisms, complex eukaryotic organisms, viruses, fungi, prions, parasites, yeasts, toxins and venoms.

A prokaryotic microorganism includes bacteria such as Gram positive, Gram negative and Gram variable bacteria and intracellular bacteria. Examples of bacteria contemplated herein include the species of the genera *Treponema* sp., *Borrelia* sp., *Neisseria* sp., *Legionella* sp., *Bordetella* sp., *Escherichia* sp., *Salmonella* sp., *Shigella* sp., *Klebsiella* sp., *Yersinia* sp., *Vibrio* sp., *Hemophilus* sp., *Rickettsia* sp., *Chlamydia* sp., *Mycoplasma* sp., *Staphylococcus* sp., *Streptococcus* sp., *Bacillus* sp., *Clostridium* sp., *Corynebacterium* sp., *Proprionibacterium* sp., *Mycobacterium* sp., *Ureaplasma* sp. and *Listeria* sp.

Particular species include *Treponema pallidum, Borrelia burgdorferi, Neisseria gonorrhea, Neisseria meningitidis, Legionella pneumophila, Bordetella pertussis, Escherichia coli, Salmonella typhi, Salmonella typhimurium, Shigella dysenteriae, Klebsiella pneumoniae, Yersinia pestis, Vibrio cholerae, Hemophilus influenzae, Rickettsia rickettsii,*

*Chlamydia trachomatis, Mycoplasma pneumoniae, Staphylococcus aureus, Streptococcus pneumoniae, Streptococcus pyogenes, Bacillus anthracis, Clostridium botulinum, Clostridium tetani, Clostridium perfringens, Corynebacterium diphtheriae, Proprionibacterium acnes, Mycobacterium tuberculosis, Mycobacterium leprae* and *Listeria monocytogenes*.

A lower eukaryotic organism includes a yeast or fungus such as but not limited to *Pneumocystis carinii, Candida albicans, Aspergillus, Histoplasma capsulatum, Blastomyces dermatitidis, Cryptococcus neoformans, Trichophyton* and *Microsporum*.

A complex eukaryotic organism includes worms, insects, arachnids, nematodes, aemobe, *Entamoeba histolytica, Giardia lamblia, Trichomonas vaginalis, Trypanosoma brucei gambiense, Trypanosoma cruzi, Balantidium coli, Toxoplasma gondii, Cryptosporidium* or *Leishmania*.

The term "viruses" is used in its broadest sense to include viruses of the families adenoviruses, Papilloma and polyomaviruses, herpesviruses: simplex, varicella-zoster, Epstein-Barr, CMV, pox viruses: smallpox, vaccinia, hepatitis B, rhinoviruses, hepatitis A, poliovirus, rubella virus, hepatitis C, arboviruses, rabies virus, influenza viruses A and B, measles virus, mumps virus, HIV, HTLV I and II.

The term "fungi" includes for example, fungi that cause diseases such as ringworm, histoplasmosis, blastomycosis, aspergillosis, cryptococcosis, sporotrichosis, coccidioidomycosis, paracoccidio-idoinycosis, and candidiasis.

The term parasite includes, but not limited to, infections caused by somatic tapeworms, blood flukes, tissue roundworms, ameba, and *Plasmodium, Trypanosoma, Leishmania*, and *Toxoplasma* species.

According to a particular and preferred embodiment, the compositions of the invention is intended for the treatment of pathologic disorder induced by pathogenic agent. Such disorders may lead to sepsis which may results in any one of ARF (acute renal failure) condition or disease such as AKI, ARDS (acute respiratory distress syndrome) and multiple system organ failure.

According to a particular and preferred embodiment, and as clearly demonstrated by Examples 3-7, the composition of the invention is particularly suitable for the treatment of ARF as demonstrated using the AKI model, which as indicated above, is a disorder which can be relieved by activation or addition of chaperones.

Acute kidney injury (AKI), formerly referred to as "acute tubular necrosis" encompasses a host of physiopathological mechanisms. Direct tubular toxicity, endothelial dysfunction with altered renal microcirculation, tubular hypoxic injury, damage from reactive oxygen species, impaired glomerular hemodynamics and localized or systemic inflammation, all interact to form renal dysfunction, characterized by acute reduction of glomerular filtration rate (GFR) and defective tubular function. Progression of chronic kidney disease (CKD) also reflects a host of physiopathological mechanisms, initiated following a primary renal structural damage. Three major instigating factors, glomerular hyperfiltration, proteinuria and renal parenchymal hypoxia lead to microvascular and nephron atrophy and to interstitial fibrosis via multiple compound and interacting mechanisms. Both AKI and the progression of CKD to end-stage renal failure lead to substantial morbidity and to markedly increased mortality, and are associated with large expenses, required for their clinical management.

Though the physiologic mechanisms associated with these disorders are only partially understood, renal parenchymal apoptotic or non-apoptotic cell death evidently plays a central role, and measures to attenuate these processes are a major goal in therapeutic interventions. One such potential intervention is the induction of cellular adaptive mechanisms, such as the upregulation of stress response genes, including heat shock proteins (HSP). These highly conserved molecules along the evolution tree act as chaperons for injured proteins throughout their proteasomal degradation [Aufricht, C. Pediatr. Nephrol. 20: 707-713 (2005)]. HSPs are considered cell protective and their induction by transient hypoxia or heat stress were shown to attenuate apoptotic damage and AKI both in vitro and in vivo [Lu, C. Y. et al. Curr. Opin. Nephrol. Hypertens. 16:83-89 (2007)].

It should be noted that all disorders indicated herein as disorders that may be treated by the compositions of the invention may also be treated by the methods of the invention described herein after.

According to another particular embodiment, the composition of the invention is provided for use in the treatment of ARF, and particularly, AKI.

As shown by Examples 2 and 7, VLP's comprising SV40 VP1 protect kidney cells from apoptosis, and may also protect cells from oxidative stress. Therefore, it should be noted that the compositions of the invention, may be further used in vitro or ex vivo for rescuing cells in a subject in need thereof from pathologic processes involving oxidative stress and apoptosis.

The term apoptosis, or programmed cell death, is a normal component of the development and health of multicellular organisms. Cells die in response to a variety of stimuli and during apoptosis, they do so in a controlled, regulated fashion. This makes apoptosis distinct from another form of cell death called necrosis in which uncontrolled cell death leads to lysis of cells, inflammatory responses and, potentially, to serious health problems. However, as indicated herein before, uncontrolled apoptotic process in some cases, may lead to pathologic disorders, for example, AKI, and thus, should be prevented. The invention therefore provides methods and compositions for attenuating harmful apoptotic process an induce cell survival pathways.

As indicated above, the composition of the invention may be applicable for conditions involving oxidative stress. Oxidative stress is caused by an imbalance between the production of reactive oxygen and a biological system's ability to readily detoxify the reactive intermediates or easily repair the resulting damage. All forms of life maintain a reducing environment within their cells. The cellular redox environment is preserved by enzymes that maintain the reduced state through a constant input of metabolic energy. Disturbances in this normal redox state can cause toxic effects through the production of peroxides and free radicals that damage all components of the cell, including proteins, lipids, and DNA. Wide variety of diseases have evidence of excess generation of free radicals, oxidative stress and inadequate antioxidant activity. Some examples are neurodegenerative diseases (see below), heart disease, HIV disease, chronic fatigue syndrome, hepatitis, cancer, autoimmune diseases, etc.

As indicated by the Examples, unpublished data of the inventors indicate that SV40 VP1 rescue cells from oxidative stress and apoptosis, probably by induction of a cell survival mechanism, preferably, the PI3K-PKB/Akt survival pathway. Therefore, according to one embodiment, the composition of the present invention may be used for inductions of cell survival pathway, preferably, the PI3K-PKB/Akt survival pathway, in cells of a subject in need thereof.

It should be noted that PKB/Akt is a key player in many cellular survival mechanisms. It has been implicated, in particular, in potential neuroprotection in neurodegenerative diseases [Schmeer, C. et al. Restor Neurol Neurosci 24:79-95 (2006)], including parkinson's disease [Fallon, L. et al. Nat. Cell. Biol. 8:834-842 (2006)], Alzheimer's disease [Cole, G. M. et al. Exp. Gerontol. 42:10-21 (2007)], and in neural survival after stroke and brain injury [Zhang, X. J. Cereb. Blood Flow Metab. 26:915-926 (2006)]. Additional examples are protection against cardiohypeprtrophy [Patten, R. D. and Karas, R. H. Trends Cardiovasc. Med. 16:69-75 (2006)] and kidney diseases [Mitch, W. E. J. Ren. Nutr. 17:66-69 (2007)].

Still further, the present invention provides a pharmaceutical composition for enhancing the ameliorating effect of chaperones on pathologic disorders.

It should be appreciated that the pharmaceutical compositions of the invention generally comprise a buffering agent, an agent which adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

In a second aspect, the present invention relates to a method for the treatment of a pathologic disorder in a subject in need thereof. This method comprises the step of administering to the treated subject a therapeutically effective amount of at least one viral capsid protein or any peptide, mutant or fragment thereof, or of VLPs comprising at least one capsid protein or any peptide, mutant or fragment thereof, or of a composition comprising the same.

The method of the invention may be applicable for treating a subject suffering from a pathologic disorder such as a neurodegenerative disorder or an autoimmune-related disorder. As used herein, the term "disorder" refers to a condition in which there is a disturbance of normal functioning. A "disease" is any abnormal condition of the body or mind that causes discomfort, dysfunction, or distress to the person affected or those in contact with the person. Sometimes the term is used broadly to include injuries, disabilities, syndromes, symptoms, deviant behaviors, and atypical variations of structure and function, while in other contexts these may be considered distinguishable categories. It should be noted that the terms "disease", "disorder", "condition" and "illness", are equally used herein.

The terms "treat, treating, treatment" as used herein and in the claims mean ameliorating one or more clinical indicia of disease activity in a patient having a pathologic disorder.

"Treatment" refers to therapeutic treatment. Those in need of treatment are mammalian subjects suffering from any pathologic disorder or an autoimmune-related disorder. By "patient" or "subject in need" is meant any mammal for which administration of the viral capsid proteins, or any pharmaceutical composition of the invention is desired, in order to prevent, overcome or slow down such infliction.

To provide a "preventive treatment" or "prophylactic treatment" is acting in a protective manner, to defend against or prevent something, especially a condition or disease.

According to one embodiment, the viral capsid protein may be any one of the capsid proteins of papillomaviruses or polyomaviruses, or any fragment, peptide, mutant, any mixtures and combinations thereof. Preferably, the viral capsid protein may be at least one of SV40 VP1, VP2, VP3, and any peptide, fragment, mutant, mixtures and combinations thereof. Most preferably, the viral capsid protein may be SV40 VP1, any peptide, mutant or fragment thereof or any VLPs comprising at SV40 VP1 or any peptide, mutant or fragment thereof. Particular embodiment relates to the SV40 VP1 protein comprising the amino acid sequence as denoted by SEQ ID NO: 1.

According to another specific embodiment, a mutated SV40 VP1 molecule may be the VP1ΔC mutant. Such mutated molecule may preferably comprise the amino acid sequence as substantially denoted by SEQ ID NO. 4.

Preferably, the pathologic disorder treated by the method of the invention are conditions caused by inactivation of cellular proteins participating in quality control processes or in inflammatory processes and therefore, may be ameliorated by activation of such cellular proteins.

According to a specifically preferred embodiment, the proteins participating in quality control processes may be chaperones. As clearly demonstrated by the invention, administration of VLP's containing VP1, or VP1 pentamers composed of the VP1ΔC mutated molecule, resulted in elevation in chaperon levels, particularly of chaperone HSP/c70. This elevation was correlated with the beneficial effect of SV40 VP1, on ARF conditions such as AKI, as clearly demonstrated by survival of treated animals, reduced blood urea and creatinine levels.

According to another embodiment, the method of the invention is intended for the treatment of a pathologic disorder such as a neurodegenerative disorder or an immune-related disorder.

According to a specific embodiment, the method of the invention is suitable for the treatment of an immune-related disorder such as an autoimmune disease, malignant and non-malignant proliferative disorders, graft rejection pathology and graft versus host disease, and disorders induced by a pathogenic agent.

In yet another specifically preferred embodiment, the method of the invention is specifically suitable for the treatment of pathologic disorder induced by pathogenic agent. Such disorders may lead to sepsis which may results in any one of ARF (acute renal failure), ARDS (acute respiratory distress syndrome) and multiple system organ failure.

Therefore, according to a specifically preferred embodiment, said ARF disease may be AKI.

As indicated herein before, acute Kidney Injury (AKI) is characterized pathologically by varying degrees of tubular cell damage. Renal cell death may result from prolonged renal ischemia, nephrotoxins, or sepsis. AKI results clinically in a rapid (hours to days) decline in the glomerular filtration rate (GFR) and tubular function that lead to retention of uremic toxins, acid-base disturbance, fluid imbalance and dysfunction of virtually all other systems.

The terms "effective amount" or "sufficient amount" as used by the methods of the invention, mean an amount necessary to achieve a selected result. The "effective treatment amount" is determined by the severity of the disease in conjunction with the preventive or therapeutic objectives, the route of administration and the patient's general condition (age, sex, weight and other considerations known to the attending physician).

Therapeutic formulations may be administered in any conventional dosage formulation. According to a particular and specific embodiment, the invention uses viral capsid proteins for the treatment of ARF, as demonstrated by the AKI model. As shown by the examples, the SV40 VP1 protein was used as VLPs, which were injected to the diseased animals. Appropriate dose may range between 0.01 to 100 mg/kg of weight, preferably, about 0.1 to 50 mg/kg, most preferably 0.1 to 20 mg/kg. Formulations typically comprise at least one active ingredient, as defined above, together with one or more acceptable carriers thereof.

As shown by the Examples, also mutated SV40 VP1 molecule, the VP1ΔC, may be used by the compositions and the methods of the invention, although higher amount may be required for achieving the desired beneficial effect on treated cells.

It should be noted that formulations used by the compositions and methods of the invention include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

In yet another embodiment, the administering step according to the method of the invention, comprises oral, intravenous, intramuscular, subcutaneous, intraperitonea, perenteral, transdermal, intravaginal, intranasal, mucosal, sublingual, topical, rectal or subcutaneous administration, or any combination thereof.

As indicated above, pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

Pharmaceutical compositions for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient.

Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol, cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). Thickeners, flavoring agents, diluents, emulsifiers, dispersing aids or binders may be desirable.

For administration by nasal inhalation, the active ingredient for use according to the present invention, which is the viral capsid proteins, or preferably, VLP's comprising SV40 VP1, or mutated VP1 molecule, may conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Thus, the pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

As indicated above, determination of a therapeutically effective amount is well within the capability of those-skilled in the art.

For any pharmaceutical composition used by the treatment method of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from in vitro cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition.

Depending on the severity and responsiveness of the condition to be treated, dosing can be of a single or a plurality of administrations, with course of treatment lasting from several days to several weeks or until cure is effected or diminution of the disease state or symptoms is achieved.

The amount of the pharmaceutical composition to be administered will of course be dependent on the subject being treated, the severity of the affliction, the manner of administration, the judgment of the prescribing physician, etc.

Although the method of the invention is particularly intended for the treatment of pathologic disorders in humans, other mammals are included. By way of non-limiting examples, mammalian subjects include monkeys, equines, cattle, canines, felines, mice, rats and pigs.

In a third aspect, the invention relates to a method for enhancing the ameliorating effect of cellular proteins participating on quality control processes, on a pathologic disorder. This method comprises the steps of contacting, ex vivo or in vitro, cells obtained from a subject suffering of a pathologic disorder with an effective amount of at least one viral capsid protein or any peptides or fragments thereof.

The invention further provides a method of enhancing the ameliorating effect of cellular proteins participating on quality control processes on a pathologic disorder in a subject in need thereof. This method comprises the step of administering to said subject, a therapeutically effective amount of at least one viral capsid protein or any peptides or fragments thereof, or of VLP's comprising the same, or of a composition comprising the same.

According to a specifically preferred embodiment, cellular proteins participating on quality control processes may be chaperones, particularly, HSP/c70.

The invention further provides a method for rescuing cells from oxidative stress or apoptosis, comprising the step of contacting cells undergoing oxidative stress or apoptotic process, with an effective amount of at least one viral capsid protein or any peptide, mutant or fragment thereof or of VLP's comprising said viral capsid protein or any peptide, mutant or fragment thereof, or of a composition comprising the same.

According to one particular embodiment, these cells are cells of a subject suffering of a pathologic disorder involving apoptotic process or oxidative stress.

The invention further provides methods for enhancing cell survival pathway, preferably, the PI3K-PKB/Akt survival pathway. The method of the invention comprises the step of contacting cells with effective amount of at least one viral capsid protein or any peptide, mutant or fragment thereof or of VLP's comprising the same. According to one particular embodiment, induction of cell survival pathway, by the methods and compositions of the invention may be performed in vitro or in vivo in cell culture, or alternatively, in vivo, in a subject in need thereof.

According to one embodiment, the viral capsid protein provided by any of the methods of the invention may be any capsid protein of papillomaviruses or polyomaviruses, or any fragment, peptides and mixtures and combinations thereof. Preferably, the viral capsid protein may be at least one of SV40 VP1, VP2, VP3, and any peptide, fragment, mutant, any mixtures and combinations thereof. Most preferably, the viral capsid protein may be SV40 VP1 or any peptide, mutant or fragment thereof, or VLP's comprising SV40 VP1. Specifically, the SV40 VP1 protein may comprise the amino acid sequence as denoted by SEQ ID NO: 1.

In yet another embodiment, the mutated VP1 molecule used by the method of the invention may be the VP1ΔC mutant, which preferably comprises the amino acid sequence as denoted by SEQ ID NO. 4.

Preferably, the method of the invention enhances the ameliorating effect of cellular proteins participating in quality control processes and therefore may be particularly used in pathologic disorder caused by inactivation of such proteins, preferably, chaperones.

According to another embodiment, the method of the invention enhances the ameliorating effect of cellular proteins, preferably, chaperones, on a pathologic disorder such as a neurodegenerative disorder or an immune-related disorder.

According to a specific embodiment, an immune-related disorder may be an autoimmune disease, malignant and non-malignant proliferative disorders, graft rejection pathology and graft versus host disease, and disorders induced by a pathogenic agent.

In yet another specifically preferred embodiment, the pathologic disorder induced by pathogenic agent may lead to sepsis which may results in any one of ARF diseases, ARDS (acute respiratory distress syndrome) and multiple system organ failure.

Therefore, according to a specifically preferred embodiment, such ARF disorder may be AKI.

In a fourth aspect, the invention relates to the use of at least one viral capsid protein or any peptide, mutant or fragment thereof in the preparation of a pharmaceutical composition for the treatment of a pathologic disorder.

According to one embodiment, the viral capsid protein used by the invention may be any capsid protein of papillomaviruses or polyomaviruses, or any fragment, mutant, peptide, mixtures and combinations thereof. Preferably, the viral capsid protein may be at least one of SV40 VP1, VP2, VP3, and any peptide, fragment, mutant, mixture and combinations thereof. Most preferably, the viral capsid protein may be SV40 VP1 or any peptide, mutant or fragment thereof.

Preferably, the use according to the invention is for the preparation of a composition which enhances the ameliorating effect of cellular proteins participating in quality control processes and therefore may be particularly used for the treatment of a pathologic disorder caused by inactivation of such proteins, preferably, of chaperones.

According to another embodiment, the use of viral capsid proteins according to the invention is for preparation of a composition for the treatment of a pathologic disorder such as a neurodegenerative disorder or an immune-related disorder.

According to a specific embodiment, an immune-related disorder may be an autoimmune disease, malignant and non-malignant proliferative disorders, graft rejection pathology and graft versus host disease, and disorders induced by a pathogenic agent.

A pathologic disorder induced by pathogenic agent may lead to sepsis which may results in any one of ARF disorder, ARDS (acute respiratory distress syndrome) and multiple system organ failure.

According to a specifically preferred embodiment, such ARF disorder may be AKI. The invention further provides the use of at least one viral capsid protein or any peptide, mutant or fragment thereof, or of VLP's comprising said capsid protein or any peptide, mutant or fragment thereof, in the preparation of a pharmaceutical composition for rescuing cells from oxidative stress or apoptosis.

According to one specific embodiment, the mutated VP1ΔC molecule may be used by the invention.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

AKI (Acute Kidney Injury) Model Animals:

AKI or as formally referred as ATN (acute tubular necrosis), are induced by the nephrotoxic agent $HgCl_2$, at a dose of 6.5 mg/kg. Injected mice developed AKI as seen by their general appearance and as measured by urea level in the blood. Blood urea levels in normal healthy animals usually range about <50 mg/dL. Blood urea significantly rises in AKI animals in the first 3-4 days. Most of the animals treated with this $HgCl_2$ dose die within 4 days. Those that survive start showing reduction in blood urea starting from day 5 and are likely to recover.

Production of VLPs

Recombinant baculovirus expressing VP1 from the polyhedrin promoter [Sandalon (1997) ibid.; Sandalon, Z. and Oppenheim, A. In SV40 protocols, L. Raptis, ed. (Totowa, N J, Humana Press Inc.) (2001)] were propagated in Sf9 cells. Briefly, high titer virus stocks (>$10^9$ pfu/ml) were used to infect logarithmic cultures of Sf9 cells, at moi 10, for VP1 production. Seventy two hours post infection the cells were harvested by centrifugation and nuclear extracts were prepared by procedures adapted from Schreiber et al. [Schreiber et al., Nucleic Acids Research 17: 6419 (1989)], or alternatively, were harvested after 5-6 days from the medium, following lysis of the infected Sf9 cells. Nuclear extracts were stored in aliquots at −80° C. Such nuclear extracts contain spontaneously assembled SV40 virus-like particles (VLPs). In order to remove macromolecules, mostly RNA, that may be trapped within the VLPs, they were disassembled and reassembled in 3 steps as follows: In step A, 5 μl Sf9 nuclear extract were treated with 1 μl of 150 mM DTT and 10 μg RNase in a final volume of 10 μl at 37° C. for 20 minutes. In step B reassembly mix (containing 10 mM ATP, 20 mM Hepes-KOH buffer at pH 7.9, 80 mM KCl, 40 mM $NH_4Cl$, 10 mM $MgCl$, 16% Glycerol and 0.08% NP-40, in a final volume of 10 μl) was added to the treated nuclear extracts (step A), and the reassembly reaction was incubated at 37° C. for 1 hour. For step C the packaging reaction was kept on ice overnight after the addition of 10 μl stabilization buffer (150 mM sodium acetate buffer pH 5.2, 3 mM $CaCl_2$, 120 mM KCl and 40 mM $NH_4Cl$, keeping the salt concentration at 160 mM), bringing the total volume to 30 μl.

The reaction mixture was treated with chloroform (5 μl), the mixture was vortexed, separated by centrifugation and partially purified VLPs recovered in the aqueous layer. VLPs were further purified and concentrated ~300 fold by stirred-ultrafiltration (to a final concentration 5-10 mg/ml) under Argon using XM300 membrane (Millipore). The concentrate was re-suspended in 0.5 M NaCl saline (half the original volume) and re-filtered 3 additional times. The purified VLPs are aliquoted and stored at −20° C. until use. Just before use the VLPs are diluted 3 fold with $H_2O$ (to a final NaCl concentration of 166 mM) and further diluted with saline to the desired VP1 concentration.

EM of Purified VLPs

Transmission electron microscopy pictures of VLPs were performed as follows: Samples were adsorbed onto formvar-carbon-coated copper grids and stained with 1% sodium phosphotungstate, pH 7.0. The samples were viewed in a Philips CM-12 electron microscope, using a voltage of 100 kV, and photographed at a magnification of 66,000×.

Purified VLPs are demonstrated by FIG. 1. As shown by the figure, in both methods of harvesting (nuclear or medium), VLP's appear as isolated nanoparticles of uniform shape and size (FIG. 1A) similar to wild type SV40 (FIG. 1B). Gel electrophoresis indicated that they contain ~95% VP1 (FIG. 1C). No DNA was detected in the particles.

Example 1

Induction/Activation of Chaperons (Hsp/c70) by SV40 LVP's

Figures 2A, 2B:
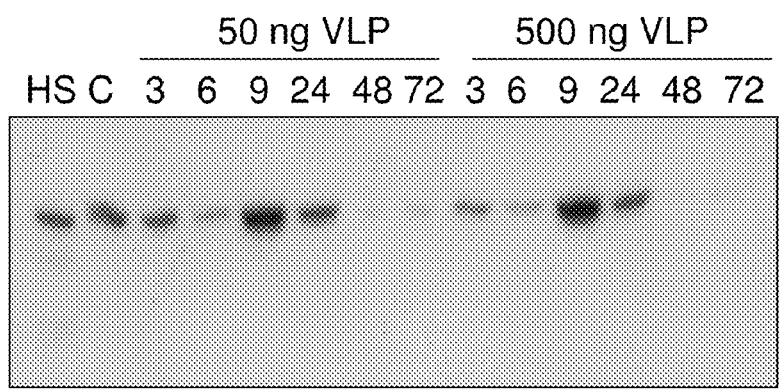
FIG. 2A-2B. SV40 VLPs Upregulate Hsp/c70 in Cultured CV1 Cells

As indicated in the background of the invention, chaperons were demonstrated as ameliorating clinical conditions such as acute tubular necrosis (ATN) or as presently defined as, AKI, and SV40 was shown to activate the expression of chaperone Hsp70. The inventors have thus examined whether SV40 capsid proteins, without any genetic material, affect or may modulate the levels of chaperone proteins such as Hsp70 for example. Therefore, the induction of chaperon biosynthesis by SV40 capsid proteins was next evaluated. SV40 capsid proteins as virus like particles (VLP's) containing VP1 only and as dissociated VP1 pentamers, were added to CV1 cells, derived from African Green monkey kidney (SV40 VLP's, 50 ng and 500 ng per $10^6$ cells). At several time points after addition of the capsid proteins, total cellular proteins were harvested and equal amounts were analyzed by polyacrylamide gel electrophoresis and Western blotting using antibodies specific to mammalian HSP/c70 chaperone. Untreated mice served as controls. FIG. 2A shows Western blot indicating levels of Hsp/c70 protein. The enhancement of HSP/c70 expression by SV40 VLPs was further analyzed. As shown by FIG. 2B, CV1 cells were treated with 50 ng VLPs, immunostained with anti-Hsp/c 70 antibody and viewed under confocal microscopy. As clearly demonstrated by the figure, Monkey CV-1 cells respond to VLP's infection by upregulating Hsp/c70. The Western analysis showed significant increase in protein level at 9 hours PI, at both concentrations of VP1 (50 and 500 ng). Confocal microscopy (FIG. 2B) showed a slight increase in the level of Hsp/c70 at 6 hours. Hsp/c70 continued to accumulate in the cells and is translocated towards the nucleus by 9 hours PI. At 48 hours Hsp/c70 is no longer seen. Similar results were obtained using the mutated VP1ΔC molecule (data not shown). The inventors therefore conclude that there is an increase in Hsp/c70, starting at 6-9 hours PI.

Example 2

SV40 VLPs Protect Cultured Kidney Cells Against Apoptosis

Accumulating evidence suggest that chaperones protect against renal failure [Lu, C. Y. et al. Curr. OP. in Nephrol. Hypertens. 16:83-89 (2007); Riordan, M. et al. Nat. Clin. Pract. Nephrol. 2:149-156 (2006); Kelly, K. J. Contrib. Nephrol. 148:86-106 (2005)]. Therefore, the inventors have next examined whether the induction of hsp/c70 by SV40 VLP's may protect cells against apoptosis. Apoptosis was induced in human kidney HEK cells by etoposide. As seen in FIG. 3, the addition of 50 ng VLPs per $10^6$ cells significantly ameliorated the apoptotic effect, and the cells appeared similar to the untreated control. Similar results were obtained with CV-1 cells.

SV40 Targets the Kidney.

The natural environment of SV40 is the primate kidney. It is therefore not surprising that the virus targets the kidneys in mice. As shown by FIGS. 4A and 4B, extensive staining can be seen with anti-VP1 antibodies in tubuli of mice 48 hours following a single tail vein injection of SV40 VLP's. Thereby, emphasizing the applicability and feasibility of treating ARF disorders using SV40 VLP's or capsid proteins.

Example 3

Establishment of a Mouse Model for Acute Kidney Injury (AKI)

The observed effect of SV40 VLP's and capsid proteins on enhancing chaperone levels and the protective effect on apoptosis in kidney cells, encouraged the inventors to further investigate the possible beneficial effect of SV40 VLP's and capsid proteins on pathologic disorders specifically related to kidney. The mercury nephrotoxicity mouse model was chosen for the initial studies because of its high reproducibility. For establishing the mouse model, BALB/C female mice, 19-21 grams (6-9 weeks), were used. $HgCl_2$, at the designated concentration, was administered IP to mice. Blood was drawn from the tail-vein on the designated day and urea was measured using Reflotron urea test (Roche). As shown in FIG. 5, the standard deviation of blood urea levels at various $HgCl_2$ concentrations is low. Based on this experiment a dose of 6.5 mg/kg $HgCl_2$ was selected for the studies of the present invention. The mortality rate at this dose in repeated experiments was consistently around 90%.

Protection of Cultured Mouse Tubular Cells from $HgCl_2$-Induced Apoptosis

In order to examine the effect of VLP's on nephrotoxicity, mouse tubular cells [Haverty, T. P. et al. J. Cell Biol. 107: 1359-1368 (1988)] were used to represent renal tubular epithelial cells affected in vivo during acute renal failure. As clearly shown in FIGS. 6A and 6B, treatment of cells with 15 μM $HgCl_2$ leads to extensive apoptosis, while infection with 50 ng VLPs/$10^6$ cells provides effective protection. Similar results were obtained for HEK and CV-1 cells (not shown).

Example 4

Treatment of Mice by VLPs Increase Survival Over a Wide Dose Range

As demonstrated above, using the AKI animal-model, most animals injected with 6.5 mg/kg $HgCl_2$ die within 3-4 days. These results were confirmed by FIG. 7A, only 2/20 (10%) of the AKI animals survived. In contrast, survival rate in the animals that received VLPs was much higher. FIG. 7A shows data of 11 animals that received VLPs in 3 injections at doses 60-600 micrograms/mouse. Survival rate of this group was 5/11 (45%). These experiments clearly demonstrate that VLPs have therapeutic effect for AKI.

To further investigate these encouraging preliminary data, the following three experimental groups were examined for analyzing the effect of VLP's on survival: the first group (Sham) received saline instead of VLP's and PBS instead of $HgCl_2$, the second group was treated with $HgCl_2$ and VLP's (AKI+VLPs), and the third group was treated with saline instead of VLPs and with $HgCl_2$. VLP's (0.3 mg/kg, in saline) were administered to mice via the tail vein in 3 consecutive daily injections (0.1 mg/kg each day, on days −3, −2, −1). Mice that did not receive VLPs were injected in parallel with saline. $HgCl_2$ in PBS was injected IP on the fourth day, counted as day 0 in the experiments shown below. Sham animals received PBS in parallel. The mice were observed for survival for 14 additional days. As shown by FIG. 7C, the treatment led to an increase in survival rate from 12% (6/49) to 63% (19/30). Statistical analysis using Kaplan-Meier/Mantel-Cox log-rank test indicated significance at P=0.000002. As shown by FIG. 7B, the attenuating effect was seen over a wide range of doses, from 3 μg/kg to 3 mg/kg.

Example 5

VP1 Pentamers are Active in Attenuation of AKI

The inventors next examined whether the entire capsids are needed for the observed beneficial effect, or whether sufficient amount of information for protection from apoptosis may be present in the VP1 pentamers. SV40 VLP's consist of 72 pentamers of the major capsid protein VP1 (360 monomers). The structure of the monomers is a β-barrel core with extending amino and carboxy-terminal arms. The pentamers are held together via the 360 carboxy-terminal arms. VP1ΔC, a mutated VP1 capsid protein deleted in the carboxy terminal arm, retains the core structure while it cannot assemble into VLPs. The deletion mutant VP1ΔC65-His [Roitman-Shemer, V. et al. Biochem Biophys. Res. Commun. 353:424-430 (2007)] was produced in Sf9 cells and purified on Ni-NTA resin (Qiagen) via the His-tag. Coomassie-stained SDS-PAGE (FIG. 8A) shows, in the lanes loaded with 1 mg protein, that the protein is about 95% pure.

Survival experiments were conducted as described above for VLPs, on small groups of mice (4 animals in each group).

As shown by FIG. 8B, VP1 treatment resulted in 75% (3/4) survival in mice injected with 0.750 mg/kg. These results indicated that VP1ΔC is also effective in protection against mercury insult, although at a higher dose when compared to VLPs.

Example 6

Effect of SV40 VLP's and Capsid Proteins on Different Disease Parameters

The inventors further investigated the applicability and feasibility of treating pathologic disorders, preferably, ARF, using SV40 VLP's, on additional kidney failure parameters. One of the parameters examined was kidney structure and morphology. Representative kidneys of the 3 groups of mice harvested on day 3 following the mercury insult are shown below. While the AKI kidneys were smaller and pale, kidneys from VLP-treated mice appeared similar to sham kidneys (FIG. 9A). The beneficial effect of VLP's was also observed when additional parameters were examined. As shown by FIG. 9B, at 4 days post infection, the increase of both serum urea and creatinine levels, two hallmarks of kidney failure, was significantly attenuated in VLP-treated AKI mice in comparison to non-treated AKI mice. Of note, serum urea in the AKI mice increased continuously during the 4 days of the experiment. In contrast, as shown by FIG. 9C, serum urea in the VLP-treated AKI animals reached a peak on day 3 and decreased thereafter. This pattern is compatible with recovery of the renal function of the VLP-treated animals and correlated with a higher survival rate.

Example 7

The Mechanism of Protection

In an attempt to analyze the possible mechanism of protection of AKI animals by SV40 VLP's and VP1 capsid protein, the involvement of stress signals was next examined.

Level of lipid peroxidation was measured by the thiobarbituric acid reactive substances (TBARS) assay [Esterbauer, H. and Cheeseman, K. H. Methods Enzymol. 186:407-421 (1990)]. The level was reduced in the VLP-treated mice (FIG. 10), suggesting that attenuation of oxidative stress by VLPs mediates, at least partially, the protection of renal function from mercury-induced nephrotoxicity.

In a parallel study (unpublished data, not shown), the inventors reveled that treatment of cells using VP1 VLPs, leads to a very rapid activation of PLC-γ and its signaling pathway. In particular, rapid activation (at 1 hour) of PARP-1 and caspases 3 and 10, suggesting initiation of apoptotic pathway. However the cell do not progress to apoptosis, and the process is stopped by the activation, at 6 hours, of chaperones (Hsp/c70) and the PI3K-PKB/Akt survival pathway, including phosphorylation of PI3K-PKB/Akt and Bad proteins. Therefore, without being bound by any theory, the inventors hypothesis that the SV40 VP1 capsid protein (or any mutant or VLP thereof) induces the PI3K-PKB/Akt survival pathway.

---

The invention claimed is:

1. A method for treatment of a disorder comprising a step of administering to a subject in need thereof a therapeutically-effective amount of a wild-type SV40 VP1 capsid protein wherein said disorder is treated and wherein said disorder is Acute Renal Failure (ARF).

2. A method for treatment of a disorder comprising a step of administering to a subject in need thereof a therapeutically-effective amount of a virus-like particle (VLP) comprising a wild-type SV40 VP1 capsid protein wherein said disorder is treated and wherein said disorder is Acute Renal Failure (ARF).

3. A method for treatment of a disorder comprising a step of administering to a subject in need thereof a therapeutically-effective amount of a pentamer comprising a wild-type SV40 VP1 capsid protein wherein said disorder is treated and wherein said disorder is Acute Renal Failure (ARF).

4. The method according to claim 1, wherein said ARF is Acute Kidney Injury (AKI).

5. The method according to claim 2, wherein said ARF is Acute Kidney Injury (AKI).

6. The method according to claim 3, wherein said ARF is Acute Kidney Injury (AKI).

7. A method for treatment of Acute Renal Failure (ARF) comprising a step of administering to a subject in need thereof a therapeutically-effective amount of a wild-type SV40 VP1 capsid protein wherein said ARF is treated.

8. A method for treatment of Acute Renal Failure (ARF) comprising a step of administering to a subject in need thereof a therapeutically-effective amount of a virus-like particle (VLP) comprising a wild-type SV40 VP1 capsid protein wherein said ARF is treated.

9. A method for treatment of Acute Renal Failure (ARF) comprising a step of administering to a subject in need thereof a therapeutically-effective amount of a pentamer comprising a wild-type SV40 VP1 capsid protein wherein said ARF istreated.

10. A method of enhancing an ameliorating effect of cellular proteins participating in quality control processes in a subject suffering from Acute Renal Failure (ARF) comprising a step of administering to the subject a therapeutically-effective amount of any one of a wild-type SV40 VP1 capsid protein, VLPs thereof, pentamers thereof, or a composition comprising the same.

11. A method for rescuing cells from oxidative stress or apoptosis and inducing survival pathways in said cells comprising a step of contacting cells undergoing oxidative stress or apoptotic process with an effective amount of any one of a wild-type SV40 VP1 capsid protein, VLPs thereof, pentamers thereof, or a composition comprising the same.

12. The method according to claim 11, wherein said cells are cells of a subject suffering from Acute Renal Failure (ARF).

* * * * *

SEQUENCE LISTING

<160> NUMBER OF SEQ ID NOS: 4

<210> SEQ ID NO 1
<211> LENGTH: 364
<212> TYPE: PRT
<213> ORGANISM: sv40 virus

<400> SEQUENCE: 1

```
Met Lys Met Ala Pro Thr Lys Arg Lys Gly Ser Cys Pro Gly Ala Ala
1               5                   10                  15

Pro Lys Lys Pro Lys Glu Pro Val Gln Val Pro Lys Leu Val Ile Lys
            20                  25                  30

Gly Gly Ile Glu Val Leu Gly Val Lys Thr Gly Val Asp Ser Phe Thr
        35                  40                  45

Glu Val Glu Cys Phe Leu Asn Pro Gln Met Gly Asn Pro Asp Glu His
    50                  55                  60

Gln Lys Gly Leu Ser Lys Ser Leu Ala Ala Glu Lys Gln Phe Thr Asp
65                  70                  75                  80

Asp Ser Pro Asp Lys Glu Gln Leu Pro Cys Tyr Ser Val Ala Arg Ile
                85                  90                  95

Pro Leu Pro Asn Leu Asn Glu Asp Leu Thr Cys Gly Asn Ile Leu Met
            100                 105                 110

Trp Glu Ala Val Thr Val Lys Thr Glu Val Ile Gly Val Thr Ala Met
        115                 120                 125

Leu Asn Leu His Ser Gly Thr Gln Lys Thr His Glu Asn Gly Ala Gly
    130                 135                 140

Lys Pro Ile Gln Gly Ser Asn Phe His Phe Phe Ala Val Gly Gly Glu
145                 150                 155                 160
```

```
Pro Leu Glu Leu Gln Gly Val Leu Ala Asn Tyr Arg Thr Lys Tyr Pro
                165                 170                 175
Ala Gln Thr Val Thr Pro Lys Asn Ala Thr Val Asp Ser Gln Gln Met
            180                 185                 190
Asn Thr Asp His Lys Ala Val Leu Asp Lys Asp Asn Ala Tyr Pro Val
        195                 200                 205
Glu Cys Trp Val Pro Asp Pro Ser Lys Asn Glu Asn Thr Arg Tyr Phe
    210                 215                 220
Gly Thr Tyr Thr Gly Gly Glu Asn Val Pro Pro Val Leu His Ile Thr
225                 230                 235                 240
Asn Thr Ala Thr Val Leu Leu Asp Glu Gln Gly Val Gly Pro Leu
            245                 250                 255
Cys Lys Ala Asp Ser Leu Tyr Val Ser Ala Val Asp Ile Cys Gly Leu
        260                 265                 270
Phe Thr Asn Thr Ser Gly Thr Gln Gln Trp Lys Gly Leu Pro Arg Tyr
    275                 280                 285
Phe Lys Ile Thr Leu Arg Lys Arg Ser Val Lys Asn Pro Tyr Pro Ile
290                 295                 300
Ser Phe Leu Leu Ser Asp Leu Ile Asn Arg Arg Thr Gln Arg Val Asp
305                 310                 315                 320
Gly Gln Pro Met Ile Gly Met Ser Ser Gln Val Glu Val Arg Val
            325                 330                 335
Tyr Glu Asp Thr Glu Glu Leu Pro Gly Asp Pro Asp Met Ile Arg Tyr
        340                 345                 350
Ile Asp Glu Phe Gly Gln Thr Thr Thr Arg Met Gln
        355                 360

<210> SEQ ID NO 2
<211> LENGTH: 33
<212> TYPE: DNA
<213> ORGANISM: artificial
<220> FEATURE:
<223> OTHER INFORMATION: DNA Primer

<400> SEQUENCE: 2
ggcggtcgac atgaagatgg ccccaacaaa aag                               33

<210> SEQ ID NO 3
<211> LENGTH: 94
<212> TYPE: DNA
<213> ORGANISM: artificial
<220> FEATURE:
<223> OTHER INFORMATION: DNA Primer

<400> SEQUENCE: 3
gctctagatc agtgatggtg atggtgatgg gtcgttggga tatcgtaatc gccctgaaaa    60
tacaggtttt ctttcacaga ccgctttcta aggg                               94

<210> SEQ ID NO 4
<211> LENGTH: 319
<212> TYPE: PRT
<213> ORGANISM: artificial
<220> FEATURE:
<223> OTHER INFORMATION: mutated SV40 VP1 mutant VP1deltaC

<400> SEQUENCE: 4

Met Lys Met Ala Pro Thr Lys Arg L

-continued

```
Gly Gly Ile Glu Val Leu Gly Val Lys Thr Gly Val Asp Ser Phe Thr
        35              40              45
Glu Val Glu Cys Phe Leu Asn Pro Gln Met Gly Asn Pro Asp Glu His
    50              55              60
Gln Lys Gly Leu Ser Lys Ser Leu Ala Ala Glu Lys Gln Phe Thr Asp
65              70              75              80
Asp Ser Pro Asp Lys Glu Gln Leu Pro Cys Tyr Ser Val Ala Arg Ile
            85              90              95
Pro Leu Pro Asn Leu Asn Glu Asp Leu Thr Cys Gly Asn Ile Leu Met
            100             105             110
Trp Glu Ala Val Thr Val Lys Thr Glu Val Ile Gly Val Thr Ala Met
        115             120             125
Leu Asn Leu His Ser Gly Thr Gln Lys Thr His Glu Asn Gly Ala Gly
        130             135             140
Lys Pro Ile Gln Gly Ser Asn Phe His Phe Phe Ala Val Gly Gly Glu
145             150             155             160
Pro Leu Glu Leu Gln Gly Val Leu Ala Asn Tyr Arg Thr Lys Tyr Pro
            165             170             175
Ala Gln Thr Val Thr Pro Lys Asn Ala Thr Val Asp Ser Gln Gln Met
            180             185             190
Asn Thr Asp His Lys Ala Val Leu Asp Lys Asp Asn Ala Tyr Pro Val
        195             200             205
Glu Cys Trp Val Pro Asp Pro Ser Lys Asn Glu Asn Thr Arg Tyr Phe
    210             215             220
Gly Thr Tyr Thr Gly Gly Glu Asn Val Pro Pro Val Leu His Ile Thr
225             230             235             240
Asn Thr Ala Thr Thr Val Leu Leu Asp Glu Gln Gly Val Gly Pro Leu
            245             250             255
Cys Lys Ala Asp Ser Leu Tyr Val Ser Ala Val Asp Ile Cys Gly Leu
            260             265             270
Phe Thr Asn Thr Ser Gly Thr Gln Gln Trp Lys Gly Leu Pro Arg Tyr
        275             280             285
Phe Lys Ile Thr Leu Arg Lys Arg Ser Val Lys Asn Glu Leu Tyr Phe
    290             295             300
Gln Gly Asp Tyr Asp Ile Pro Thr Thr His His His His His His
305             310             315
```